United States Patent
Zhou et al.

(10) Patent No.: US 10,117,390 B2
(45) Date of Patent: Nov. 6, 2018

(54) USE OF GENIC MALE STERILITY GENE AND MUTATION THEREOF IN HYBRIDIZATION

(71) Applicant: XINGWANG INVESTMENT CO., LTD, Changping District, Beijing (CN)

(72) Inventors: Junli Zhou, Beijing (CN); Ying Wang, Beijing (CN)

(73) Assignee: XINGWANG INVESTMENT CO., LTD., Beijing (CN)

( * ) Notice: Subject to any disclaimer, the term of this patent is extended or adjusted under 35 U.S.C. 154(b) by 28 days.

(21) Appl. No.: 14/917,477

(22) PCT Filed: Sep. 15, 2014

(86) PCT No.: PCT/CN2014/086505
§ 371 (c)(1),
(2) Date: Mar. 8, 2016

(87) PCT Pub. No.: WO2015/035951
PCT Pub. Date: Mar. 19, 2015

(65) Prior Publication Data
US 2016/0255782 A1 Sep. 8, 2016

(30) Foreign Application Priority Data
Sep. 16, 2013 (CN) .......................... 2013 1 0421770

(51) Int. Cl.
C12N 15/63 (2006.01)
C12N 15/82 (2006.01)
A01H 1/02 (2006.01)
A01H 5/10 (2018.01)
C07K 14/415 (2006.01)

(52) U.S. Cl.
CPC ................. *A01H 1/02* (2013.01); *A01H 5/10* (2013.01); *C07K 14/415* (2013.01); *C12N 15/63* (2013.01); *C12N 15/82* (2013.01); *C12N 15/8289* (2013.01)

(58) Field of Classification Search
None
See application file for complete search history.

(56) References Cited

U.S. PATENT DOCUMENTS

2007/0209085 A1* 9/2007 Wu ...................... C12Q 1/6895
800/278

FOREIGN PATENT DOCUMENTS

| CN | 102250947 | 11/2011 |
|---|---|---|
| CN | 102732556 | 10/2012 |
| WO | 2008/112970 | 9/2008 |

OTHER PUBLICATIONS

International Search Report of International Application No. PCT/CN2014/086505 dated Feb. 4, 2015.
Genbank: NM_001196367.1, "*Zea mays* uncharacterize LOC100501692, mRNA", Genbank, 2013.

* cited by examiner

*Primary Examiner* — Phuong T Bui
(74) *Attorney, Agent, or Firm* — Michael Ye; Morris, Manning & Martin, LLP

(57) ABSTRACT

The present invention belongs to the field of biotechnology, in particular to a hybrid breeding method for maize, which comprises sterile line reproduction and hybrid seed production, and more particularly to plant FL1 gene or alleles thereof, as well as mutant plants produced by the variation of the gene.

12 Claims, 4 Drawing Sheets
Specification includes a Sequence Listing.

Figure 10

SEQUENCE LISTING

<160> NUMBER OF SEQ ID NOS: 20

<210> SEQ ID NO 1
<211> LENGTH: 2585
<212> TYPE: DNA
<213> ORGANISM: Zea mays L.

<400> SEQUENCE: 1

```
ctcacagcaa attcgtctca cgcatattcg tcatccagct ccgtttaaaa tgcgtgctca        60
ttatccctca agcatgcata tactatatat gatgcagatc atatatgacc tttatacaat       120
tatcaccacc tcgattcctc gcggcacatc tttgcaccgc agaacgaccg tgcagtattt       180
```

```
tatacaaaca tctactctcg atctacccat gagctaactc ccaatatata agcgagccga    240
acttttctcc tatctgagca ctgctgctgc tgaaaatggc gcctgggctt gcgaactggg    300
tcgcgctggt tctgaccgtc ctccttggtc tctcgtgcct cgtcgtcgcg ctctcggagg    360
atggtttgtg ccggacttgt cacgcgctct ttggtatttc tgcagttctg caaacgtgtg    420
aattggcatg gacatgtgca gaaacactgg acaagctgcg gttcgtgcgc cacgcacagg    480
acgcgcccct ggtgtcgcag tacaactaca tcgtgatcgg cggcggcacg gcggggtgcc    540
cgctggcggc gacgctgtcg gagcactcgc gcgtgctgct cctggagcgc ggggcctcc     600 cgtcccgcaa catgtccgac cagcagcact tcacggacgc gctggcggac acgtccccgg    660
cgtcgcccgc gcagcggttc gtgtccgagg acggcgtggt gaacgcgcgg gcccgggtgc    720
tgggcggggg cagctgcctc aacgccgggt tctacacgcg ggccagcacc gactacgtgc    780
gcgccgccgg ctgggacgcc cgcctcgtca actcgtccta ccgctgggtg gagcgcgcgc    840
tcgtgttccg ccccgccgtg ccccgtggc  aggccgcgct ccgcgacgcg ctgctcgagg    900
ccggcgtcac gcccgacaac ggcttcacct tcgaccacgt cacgggcacc aagatcgggg    960
gcaccatctt cgacagcagc ggccagcgcc acaccgccgc cgacttcctc cgccacgcgc   1020
gccccagggg gctcaccgtg ttcctctacg ctaccgtctc caggatcctc ttcagacagc   1080
aaggtacgta cgtgcgtgca cggcttccgc atttttttt  cgacagtgcg ggctggcacg   1140
atcgcgctct gaagcggaga atcgtgcgct gtcgacagag ggcgtgccgt acccggtggc   1200
gtacggtgtg gtgttcacgg acccgctcgg ggtgcagcac cgggtgtacc tccgggacgg   1260
cgccaagaac gaggtgatcc tgtcggcggg gacgctgggg agcccgcagc tgctgatgct   1320
gagcggcgtc ggcccgcagg cgcacctgga ggcgcacggc gtccaggtgc tggtggacca   1380
gcccatggtc gggcagggcg tggctgacaa cccgatgaac tcggtgttca tcccgtcgcc   1440
ggtgcccgtc acgctgtcgc tcgtgcaggt cgtcgggatc acccggtccg gcagcttcat   1500
cgagggcgtg agcggctccg agttcggcat ccccgtctcc gagggcgccc gtcgcctggc   1560
tcgcagcttc ggcctcttct ctccgcagac ggggcagctg gcacgttgc  cgccgaagca   1620 gagaaccca  gaggccctgg agcgcgcggc ggaggcgatg cggcggctgg acaggcgggc   1680
gttccggggc ggattcatcc tggagaagat cctgggcccc gtctcctcgg gccacgtcga   1740
gctgcggtcc gccgacccgc gcgcgaaccc ggcggtgacg ttcaactact tccaggagtc   1800
ggaggacctg cagcggtgcg tgcgcggcat ccagacgatc gagcgcgtga tccagtcccg   1860
ggccttcgcc aacttcacct acgccaacgc ttcacggag  tccatcttca ccgactccgc   1920
caacttcccc gtcaacctcc tgccgcggca cgtcaacgac tcccggacgc ccgagcagta   1980
ctgcagggac accgtcatga ccatctggca ttaccacggc gggtgccagg tcggcgccgt   2040
cgtggacgac gattaccggg tgttcggcgt gcagcgactg agggtgatcg acagctccac   2100
gttcaagtac tccccccggca ccaacccgca ggccaccgtc atgatgctcg aaggtatat   2160 gggtgtgaaa attcaggccg agagatggag gaaatgatcg agatttcaag tttcagcatg   2220 gtctaggac  taggcctcta gctgtgataa tgaatatcaa tcaacacatc tgtaactggg   2280
taactgctct agcctctaga gtaggtttta ttttctcta  gatatttttt taatctcctc   2340
tagacatact cctagcttcc gcatgttgtt ggttccattt caccacaccc ctagatgcat   2400
tgttcagcat ttcgcgggaa taatgagaat tatgctgaaa aggcatgatc gctcctcctg   2460
cctattctac agaaaattaa ataaagaacc gccatttcat caaataaacc aaaggccgtg   2520
```

```
ttctgtggat tggaagggat cgaggaagat taaatcgttt ctatttaatt ttcccttaat    2580
tttaa                                                                2585

<210> SEQ ID NO 2
<211> LENGTH: 1827
<212> TYPE: DNA
<213> ORGANISM: Zea mays L.

<400> SEQUENCE: 2
atggcgcctg ggcttgcgaa ctgggtcgcg ctggttctga ccgtcctcct tggtctctcg      60
tgcctcgtcg tcgcgctctc ggaggatggt ttgtgccgga cttgtcacgc gctctttggt     120
atttctgcag ttctgcaaac gtgtgaattg catggacat gtgcagaaac actggacaag      180
ctgcggttcg tgcgccacgc acaggacgcg cccctggtgt cgcagtacaa ctacatcgtg     240
atcggcggcg gcacggcggg gtgcccgctg gcggcgacgc tgtcggagca ctcgcgcgtg     300
ctgctcctgg agcgcggggg cctcccgtcc cgcaacatgt ccgaccagca gcacttcacg     360
gacgcgctgg cggacacgtc cccggcgtcg cccgcgcagc ggttcgtgtc cgaggacggc     420
gtggtgaacg cgcggggccc ggtgctgggc gggggcagct gcctcaacgc cgggttctac     480
acgcgggcca gcaccgacta cgtgcgcgcc gccggctggg acgcccgcct cgtcaactcg     540
tcctaccgct gggtggagcg cgcgctcgtg ttccgccccg ccgtgccccc gtggcaggcc     600
gcgctccgca cgcgctgct cgaggccggc gtcacgcccg acaacggctt cacctttcgac     660 cacgtcacgg gcaccaagat cgggggcacc atcttcgaca gcagcggcca gcgccacacc     720
gccgccgact cctccgcca cgcgcgcccc aggggggctca ccgtgttcct ctacgctacc     780
gtctccagga tcctcttcag acagcaagag ggcgtgccgt accggtggc gtacggtgtg     840 gtgttcacga cccgctcgg ggtgcagcac cgggtgtacc tccgggacgg cgccaagaac     900
gaggtgatcc tgtcggcggg gacgctgggg agcccgcagc tgctgatgct gagcggcgtc     960
ggcccgcagg cgcacctgga ggcgcacggc gtccaggtgc tggtggacca gcccatggtc    1020
gggcagggcg tggctgacaa cccgatgaac tcggtgttca tcccgtcgcc ggtgcccgtc    1080
acgctgtcgc tcgtgcaggt cgtcgggatc acccggtccg gcagcttcat cgagggcgtg    1140
agcggctccg agttcggcat ccccgtctcc gagggcgccc gtcgcctggc tcgcagcttc    1200
ggcctcttct ctccgcagac ggggcagctg ggcacgttgc cgccgaagca gagaacccca    1260
gaggccctgg agcgcgcggc ggaggcgatg cggcggctgg acaggcgggc gttccggggc    1320
ggattcatcc tggagaagat cctgggcccc gtctcctcgg gccacgtcga gctgcggtcc    1380
gccgacccgc gcgcgaaccc ggcggtgacg ttcaactact tccaggagtc ggaggacctg    1440
cagcggtgcg tgcgcggcat ccagacgatc gagcgcgtga tccagtcccg gcccttcgcc    1500
aacttcacct acgccaacgc ttccacggag tccatcttca ccgactccgc caacttcccc    1560
gtcaacctcc tgccgcggca cgtcaacgac tcccggacgc ccgagcagta ctgcagggac    1620
accgtcatga ccatctggca ttaccacggc gggtgccagg tcggcgccgt cgtggacgac    1680
gattaccggg tgttcggcgt gcagcgactg agggtgatcg acagctccac gttcaagtac    1740 tccccggca ccaacccgca ggccaccgtc atgatgctcg aaggtatat gggtgtgaaa     1800 attcaggccg agagatggag gaaatga                                       1827

<210> SEQ ID NO 3
<211> LENGTH: 608
<212> TYPE: PRT
<213> ORGANISM: Zea mays L.
```

<400> SEQUENCE: 3

```
Met Ala Pro Gly Leu Ala Asn Trp Val Ala Leu Val Leu Thr Val Leu
1               5                   10                  15

Leu Gly Leu Ser Cys Leu Val Ala Leu Ser Glu Asp Gly Leu Cys
            20                  25                  30

Arg Thr Cys His Ala Leu Phe Gly Ile Ser Ala Val Leu Gln Thr Cys
            35                  40                  45

Glu Leu Ala Trp Thr Cys Ala Glu Thr Leu Asp Lys Leu Arg Phe Val
    50                  55                  60

Arg His Ala Gln Asp Ala Pro Leu Val Ser Gln Tyr Asn Tyr Ile Val
65                  70                  75                  80

Ile Gly Gly Gly Thr Ala Gly Cys Pro Leu Ala Ala Thr Leu Ser Glu
                85                  90                  95

His Ser Arg Val Leu Leu Leu Glu Arg Gly Gly Leu Pro Ser Arg Asn
            100                 105                 110

Met Ser Asp Gln Gln His Phe Thr Asp Ala Leu Ala Thr Ser Pro
            115                 120                 125

Ala Ser Pro Ala Gln Arg Phe Val Ser Glu Asp Gly Val Val Asn Ala
130                 135                 140

Arg Ala Arg Val Leu Gly Gly Ser Cys Leu Asn Ala Gly Phe Tyr
145                 150                 155                 160

Thr Arg Ala Ser Thr Asp Tyr Val Arg Ala Gly Trp Asp Ala Arg
                165                 170                 175

Leu Val Asn Ser Ser Tyr Arg Trp Val Glu Arg Ala Leu Val Phe Arg
            180                 185                 190

Pro Ala Val Pro Pro Trp Gln Ala Ala Leu Arg Asp Ala Leu Leu Glu
            195                 200                 205

Ala Gly Val Thr Pro Asp Asn Gly Phe Thr Phe Asp His Val Thr Gly
            210                 215                 220

Thr Lys Ile Gly Gly Thr Ile Phe Asp Ser Ser Gly Gln Arg His Thr
225                 230                 235                 240

Ala Ala Asp Phe Leu Arg His Ala Arg Pro Arg Gly Leu Thr Val Phe
                245                 250                 255

Leu Tyr Ala Thr Val Ser Arg Ile Leu Phe Arg Gln Gln Glu Gly Val
            260                 265                 270

Pro Tyr Pro Val Ala Tyr Gly Val Val Phe Thr Asp Pro Leu Gly Val
            275                 280                 285

Gln His Arg Val Tyr Leu Arg Asp Gly Ala Lys Asn Glu Val Ile Leu
            290                 295                 300

Ser Ala Gly Thr Leu Gly Ser Pro Gln Leu Leu Met Leu Ser Gly Val
305                 310                 315                 320

Gly Pro Gln Ala His Leu Glu Ala His Gly Val Gln Val Leu Val Asp
                325                 330                 335

Gln Pro Met Val Gly Gln Gly Val Ala Asp Asn Pro Met Asn Ser Val
            340                 345                 350

Phe Ile Pro Ser Pro Val Pro Val Thr Leu Ser Leu Val Gln Val Val
            355                 360                 365

Gly Ile Thr Arg Ser Gly Ser Phe Ile Glu Gly Val Ser Gly Ser Glu
            370                 375                 380

Phe Gly Ile Pro Val Ser Glu Gly Ala Arg Arg Leu Ala Arg Ser Phe
385                 390                 395                 400

Gly Leu Phe Ser Pro Gln Thr Gly Gln Leu Gly Thr Leu Pro Pro Lys
```

```
                    405                 410                 415
Gln Arg Thr Pro Glu Ala Leu Glu Arg Ala Ala Glu Ala Met Arg Arg
                420                 425                 430

Leu Asp Arg Arg Ala Phe Arg Gly Gly Phe Ile Leu Glu Lys Ile Leu
            435                 440                 445

Gly Pro Val Ser Ser Gly His Val Glu Leu Arg Ser Ala Asp Pro Arg
        450                 455                 460

Ala Asn Pro Ala Val Thr Phe Asn Tyr Phe Gln Glu Ser Glu Asp Leu
465                 470                 475                 480

Gln Arg Cys Val Arg Gly Ile Gln Thr Ile Glu Arg Val Ile Gln Ser
                485                 490                 495

Arg Ala Phe Ala Asn Phe Thr Tyr Ala Asn Ala Ser Thr Glu Ser Ile
            500                 505                 510

Phe Thr Asp Ser Ala Asn Phe Pro Val Asn Leu Leu Pro Arg His Val
        515                 520                 525

Asn Asp Ser Arg Thr Pro Glu Gln Tyr Cys Arg Asp Thr Val Met Thr
    530                 535                 540

Ile Trp His Tyr His Gly Gly Cys Gln Val Gly Ala Val Val Asp Asp
545                 550                 555                 560

Asp Tyr Arg Val Phe Gly Val Gln Arg Leu Arg Val Ile Asp Ser Ser
                565                 570                 575

Thr Phe Lys Tyr Ser Pro Gly Thr Asn Pro Gln Ala Thr Val Met Met
            580                 585                 590

Leu Gly Arg Tyr Met Gly Val Lys Ile Gln Ala Glu Arg Trp Arg Lys
        595                 600                 605

<210> SEQ ID NO 4
<211> LENGTH: 875
<212> TYPE: DNA
<213> ORGANISM: Zea mays L.

<400> SEQUENCE: 4
gaggaagatg aggatgagat cgaggagttc gattagagtt atgtaatttt attttgatta      60
taatataatt ttgtttaatt attatgcact ttgtaatttt taagtcaata aaaatattgt     120
gttgtgtgat ttctgagtgt tgaaataaat ctgcgtgaat tacttaattt tgaaatataa     180
aagctgatgt ggctataggc tgaggttata gcctcctaca gtttgtgcac tgaaatagct     240
ggaacgagag tggagtcgag aggtgacgtg gggggggcg agagtgaggc tatccaggat      300
taaggtgcag cctgcaggga tgcaaatcct agataccagg accagaactt cttaacgacc     360
gccggtaaaa tttactcagg ttattctcgt ctaaaaagaa ttaagtagga ttttaacttg     420
tttatgattt aatctcactc aatctgctct aatctcatg gtttgggtat aaaacgaaca      480
tgccctaaat aaattagaaa cactacatac atatacatct ccatgtatta aaggcatgcg     540
cttgctactg ctacctgcga aatattatca agaatggcaa gtaaactccc ctgcttggtg     600
ctcacagcaa attcgtctca cgcatattcg tcatccagct ccgtttaaaa tgcgtgctca     660
ttatccctca agcatgcata tactatatat gatgcagatc atatatgacc tttatacaat     720
tatcaccacc tcgattcctc gcggcacatc tttgcaccgc agaacgaccg tgcagtattt     780
tatacaaaca tctactctcg atctacccat gagctaactc ccaatatata agcgagccga     840 actttttctcc tatctgagca ctgctgctgc tgaaa                               875

<210> SEQ ID NO 5
<211> LENGTH: 2500
```

<212> TYPE: DNA
<213> ORGANISM: Zea mays L.

<400> SEQUENCE: 5

```
gagggaggcg atgcgctgga cgggcgggtg cgtgggcgag agcgtggggc aagagcgagc    60
tagcacgatc tgattggtcc acgtggcacc acgtgtgcta gccattgcaa ctagcctttt   120
ttacagtttg gagtccaaaa aattcaaaaa atgcaaaaaa tcacaaaatt catccccaat   180
ccctgtataa ataccctac cgtggtggag ctcattacac agaccatttt atctcatttt    240
ctcttccaaa ctcccctctc ttcacacaat gttgggttgg tccccagatt tgaacacctt   300
cacggatctc ttgcaatccg atgggtcacc tacaacccct tccgtttgatg agtcttcttt   360
actacatcac cactccgatg tttcagcccc agtcccccat gcactagttc cggctgcgcg   420
tccaccatca tacccttatc cctaccattt ctattaatat ccattgtctt catatggtca   480
acctccaact tcccaagatg gaattcaagc ttcattccca gtacgtccgt ataccctcc    540
cccacctgct gtggatggaa gtcaagcttc ttttcaggta cctatgtatg ccctcctcca   600
tatgctccac ctttgtatgg agtacctcct tatgttccat atgctccatc tccgtatgga   660
gcacctcatc catatgctcc accttcgtat ggagcacctc ctccagttgc acctttatct   720
gttggatcca aaaccaagc tgaggaaaat cctgtgccga aggaaaagtg ccccaaaagg    780
ctagattgga cgactaccga cgagaaaaag ttggtgagtg aatcatttct catttattta   840
atcttgattt ttttagttta cttacattat aggttttatt ataggccaat gctcggatta   900
tgcattctaa tgatcccatc tccggcaaca ataagagtga atcaagtttc tggggtcaaa   960
tagcggtagc atataactcc atctccgacc ctctccgtcg tcaaaccggc aagcaactta  1020
aagatcattg ggtcacctac aaccgggagg tgaccaagtt caatggatac tacctcaaag  1080
aagaaaggtt gcgtcagagc ggaacaaacg atgcaatggt catggaggca gcagtggcga  1140
ggttcgaggg taaaatgggg catccatta agcaccatca ctggtggcaa gttgttcgcc   1200
acgagcccaa gtggtcagca aagcatagtc ttggtagtgg atttgacacg actgtgaata  1260
agagaacccg agtcggagta tctggtgaat atagttctgg aggcactgaa gacaccgagg  1320
aggaagtgcc tcgaccagtg aggcgttata gtgcaaaggc agctacgcga aagacaaaga  1380
cgaaggggaa aaggaaggaa cccacgagca gcggatcaac aagtgaagca ttcaaaatga  1440
agaacatgtg gggtggatta gtgaaggcca aacttttgaa gcaatggaac atcctaaagg  1500
gccgatcaac cagggatatg aacccggctg aaagacgtat ccatgccgga gctgtaaaga  1560
tggtcgaaaa agaatttggt ttggtagatg acaaagaaga gaaatcggaa gcaggacgtg  1620
aataggagga agatgaggat gagatcgagg agttcgatta gagttatgta attttatttt  1680
gattataata taatttgtt taattattat gcactttgta atttttaagt caataaaaat   1740
attgtgttgt gtgatttctg agtgttgaaa taaatctgcg tgaattactt aattttgaaa  1800
tataaaagct gatgtggcta taggctgagg ttatagcctc ctacagtttg tgcactgaaa  1860
tagctggaac gagagtggag tcgagaggtg acgtgggagg gggcgagagt gaggctatcc  1920
aggattaagg tgcagcctgc agggatgcaa atcctagata ccaggaccag aacttcttaa  1980
cgaccgccgg taaaatttac tcaggttatt ctcgtctaaa aagaattaag taggatttta  2040
acttgtttat gatttaatct cactcaatct gctctaatct acatggtttg ggtataaaac  2100
gaacatgccc taaataaatt agaaacacta catacatata catctccatg tattaaaggc  2160
atgcgcttgc tactgctacc tgcgaaatat tatcaagaat ggcaagtaaa ctcccctgct  2220
```

| | | | | |
|---|---|---|---|---|
| tggtgctcac | agcaaattcg | tctcacgcat | attcgtcatc | cagctccgtt taaaatgcgt | 2280 |
| gctcattatc | cctcaagcat | gcatatacta | tatatgatgc | agatcatata tgaccttat | 2340 |
| acaattatca | ccacctcgat | tcctcgcggc | acatctttgc | accgcagaac gaccgtgcag | 2400 |
| tattttatac | aaacatctac | tctcgatcta | cccatgagct | aactcccaat atataagcga | 2460 |
| gccgaacttt | tctcctatct | gagcactgct | gctgctgaaa | | 2500 |

<210> SEQ ID NO 6
<211> LENGTH: 3041
<212> TYPE: DNA
<213> ORGANISM: Oryza sativa

<400> SEQUENCE: 6

| | | | | |
|---|---|---|---|---|
| attcaagaca | tctactcttg | atctaccatt | gagctaactc | cggatatata aacagaccga | 60 |
| acgtttcgtc | ccaggggaat | gtgaaagtta | gcgaatttgc | ccggcgaaaa tggcagcact | 120 |
| tggccgcgcg | agctcgtcgg | cgccggtgct | tgccgccgcc | gccgccgtgc tcctctcgct | 180 |
| ctgcctcgcc | gcgctctcgg | aagagcaagg | tgcgtaaacg | ttgcgttgta tctttgcgtt | 240 |
| gatgcgtgtt | gcgtcgtcgt | cgtgttcatg | gcgtgcgatg | gcgttgtgca gagcaactgg | 300 |
| agaacctgcg | gttcgtgcgg | cacgcgcagg | acgcgccgct | ggtgtcgagc tacaactaca | 360 |
| tcgtcatcgg | cggcggcacg | gcggggtgcc | cgctggcggc | gacgctgtcg gagcactcgc | 420 |
| gcgtgctgct | gctggagcgc | ggcggcctgc | cgtacgccaa | catgtcgagc gagcagcact | 480 |
| tcacggacgc | gctggccgac | acgtcgccgg | cgtcgccggc | gcagcggttc atctcggagg | 540 |
| acggcgtggt | gaacgcccgg | gcgcgggtgc | tcggcggcgg | gagctgcctc aacgccgggt | 600 |
| tctacacgcg | ggcgagcaac | gagtacgtgc | gcgcctccgg | gtgggacgcg cggctggtga | 660 |
| actcgtcgta | ccggtgggtg | gagcgctcgc | tggtgttccg | ccccgacgtg ccgccgtggc | 720 |
| aggcggcgct | ccgcgacgcg | ctgctcgagg | tcggcgtcac | gcccgacaac ggcttcacct | 780 |
| tcgaccacgt | caccggcacc | aagatcggcg | gcaccatctt | cgacaactcc ggccagcgcc | 840 |
| acaccgccgc | cgacttcctc | cgccacgccc | gccccgcgg | cctcaccgtc tcctctacg | 900 |
| ccaccgtctc | ccgtatcctc | ttcaaaagcc | aaggtacaca | gctacgatga aaatggaaaa | 960 |
| tgtgctgtgc | gccgaagaag | cttgacctca | cgacggcgag | cttttgccat ggcgtgcaga | 1020 |
| cggggtgccg | tacccggtgg | cgtacggggt | ggtgttctcg | gacccgctgg gggtgcagca | 1080 |
| ccgggtgtac | ctccgcgacg | gcgacaagaa | cgaggtgatc | gtgtcggcgg ggacgctggg | 1140 |
| gagcccgcag | ctgctgatgc | tgagcggcgt | cgggccgcag | gcgcacctgg aggcgcacgg | 1200 |
| catcgaggtg | atcgtggacc | aacccatggt | cgggcagggc | gtcgccgaca acccgatgaa | 1260 |
| ctcggtgttc | atcccgtcgc | cggtgccggt | ggagctctcc | ctggtgcagg tcgtcggcat | 1320 |
| cacccgctcc | ggcagcttca | tcgagggggt | gagcgggtcg | gagttcggca tgccggtgtc | 1380 |
| ggacggcgcg | ctccgtggg | cgcgcagctt | cgggatgctg | tcgccgcaga cggggcagct | 1440 |
| cggcacgctg | ccgccgaagc | agaggacgcc | ggaggcgctg | cagcgggcgg cggaggcgat | 1500 |
| gatgcggctg | gacaggaggg | cgttccgggg | aggcttcatc | ctggagaaga tcctcgggcc | 1560 |
| ggtgtcctcc | ggccacgtcg | agctgcgaac | caccgaccg | agggcgaacc cgtcggtgac | 1620 |
| gttcaactac | ttccgcgagg | cagaggatct | ggagcggtgc | gtccatggca tcgagacgat | 1680 |
| cgagcgggtg | atccagtcgc | gggccttctc | caacttcacc | tacgccaacg cctccgtcga | 1740 |
| gtccatcttc | accgattccg | ccaacttccc | cgtcaacctg | ctgccgcgcc atgtcaacga | 1800 |
| ctcgcgctcg | ccggagcagt | actgcatgga | caccgtcatg | accatctggc actaccacgg | 1860 |

```
cggctgccat gtcggcgccg tcgtcgacga cgattaccgg gtgttcgggg tgcaggggct    1920
cagggtgatc gacagctcca ccttcaagta ctcccccggc accaaccctc aggccaccgt    1980
catgatgctc ggcaggtaac tggcatcatt ttagctcatg aaagtgcatt gccatgagta    2040
acaacacact aacagtatag ttttcaatat ggacactggg caggtatatg ggtgtgaaga    2100
ttcagtccga gagatggaag aaatgatgaa caaaagataa tttcgtttca ggagcaaaaa    2160
aatgcatgta attcaaggaa aagaaaatgt tcaactgtct ttagagttta gagtagattt    2220
tatttgcacc cacttaattt ttactcttct ctagacatag gttcagtatc tgcttgttga    2280
ttatgtaacc ttgaagaagc attgcaaaaa caaagcggaa acttatgtta ccaagggcat    2340
gacgaagaaa taatggatt agatttcatt gacacttaga aaatggaacc agcaaatcaa     2400
ggctgaaaat aattcacta gaaacttatt ttaatggctt acatgtcgc tacatactta      2460 aatcaatcaa agttgctacc aaagccatgt tccctaaaca gagggttccg ggctttcaaa    2520
cattcttaat cttctataca ttgataaaaa gtatacataa aaagaaaacc tattaagatg    2580
gaaatgttga attctcttaa gaaaggcata aaaaatgcag ggtaataacc ttttcttgtc    2640
atgtcctact tggtttcaac ctatattgct agcaaaattt tcacgctatc tataacctca    2700
ggaagcagaa tagctcagaa tcactagcaa ttgtatactt acagataatc gaaattcata    2760
ttgtgaggtt ttcttggatg gctcggaatg atccacagat gttaccaccc atgtctggga    2820
atgacgtaca tcctggcaag ggtttcacct tgcccttacg gtcaacactt acagggtact    2880
tcattaggtg gcctctcatc tcagtcacct cattatcaac aaatcgttcc cagttctgtt    2940
caccgatttg gcgaactcgt ctcatgcatt ccatggtctc tggatagttg aagccttcct    3000
caaccactcc aatatgctcc gcccaaagag acattctgta c                        3041
```

<210> SEQ ID NO 7
<211> LENGTH: 586
<212> TYPE: PRT
<213> ORGANISM: Oryza sativa L.

<400> SEQUENCE: 7

```
Met Ala Ala Leu Gly Arg Ala Ser Ser Ser Ala Pro Val Leu Ala Ala
1               5                   10                  15

Ala Ala Ala Val Leu Leu Ser Leu Cys Leu Ala Ala Leu Ser Glu Glu
            20                  25                  30

Gln Glu Gln Leu Glu Asn Leu Arg Phe Val Arg His Ala Gln Asp Ala
        35                  40                  45

Pro Leu Val Ser Ser Tyr Asn Tyr Ile Val Ile Gly Gly Gly Thr Ala
    50                  55                  60

Gly Cys Pro Leu Ala Ala Thr Leu Ser Glu His Ser Arg Val Leu Leu
65                  70                  75                  80

Leu Glu Arg Gly Gly Leu Pro Tyr Ala Asn Met Ser Ser Glu Gln His
                85                  90                  95

Phe Thr Asp Ala Leu Ala Asp Thr Ser Pro Ala Ser Pro Ala Gln Arg
            100                 105                 110

Phe Ile Ser Glu Asp Gly Val Val Asn Ala Arg Ala Arg Val Leu Gly
        115                 120                 125

Gly Gly Ser Cys Leu Asn Ala Gly Phe Tyr Thr Arg Ala Ser Asn Glu
    130                 135                 140

Tyr Val Arg Ala Ser Gly Trp Asp Ala Arg Leu Val Asn Ser Ser Tyr
145                 150                 155                 160
```

```
Arg Trp Val Glu Arg Ser Leu Val Phe Arg Pro Asp Val Pro Pro Trp
                165                 170                 175
Gln Ala Ala Leu Arg Asp Ala Leu Leu Glu Val Gly Val Thr Pro Asp
            180                 185                 190
Asn Gly Phe Thr Phe Asp His Val Thr Gly Thr Lys Ile Gly Gly Thr
        195                 200                 205
Ile Phe Asp Asn Ser Gly Gln Arg His Thr Ala Ala Asp Phe Leu Arg
    210                 215                 220
His Ala Arg Pro Arg Gly Leu Thr Val Leu Leu Tyr Ala Thr Val Ser
225                 230                 235                 240
Arg Ile Leu Phe Lys Ser Gln Asp Gly Val Pro Tyr Pro Val Ala Tyr
                245                 250                 255
Gly Val Val Phe Ser Asp Pro Leu Gly Val Gln His Arg Val Tyr Leu
            260                 265                 270
Arg Asp Gly Asp Lys Asn Glu Val Ile Val Ser Ala Gly Thr Leu Gly
        275                 280                 285
Ser Pro Gln Leu Leu Met Leu Ser Gly Val Gly Pro Gln Ala His Leu
    290                 295                 300
Glu Ala His Gly Ile Glu Val Ile Val Asp Gln Pro Met Val Gly Gln
305                 310                 315                 320
Gly Val Ala Asp Asn Pro Met Asn Ser Val Phe Ile Pro Ser Pro Val
                325                 330                 335
Pro Val Glu Leu Ser Leu Val Gln Val Val Gly Ile Thr Arg Ser Gly
            340                 345                 350
Ser Phe Ile Glu Gly Val Ser Gly Ser Glu Phe Gly Met Pro Val Ser
        355                 360                 365
Asp Gly Ala Leu Arg Trp Ala Arg Ser Phe Gly Met Leu Ser Pro Gln
    370                 375                 380
Thr Gly Gln Leu Gly Thr Leu Pro Pro Lys Gln Arg Thr Pro Glu Ala
385                 390                 395                 400
Leu Gln Arg Ala Ala Glu Ala Met Met Arg Leu Asp Arg Arg Ala Phe
                405                 410                 415
Arg Gly Gly Phe Ile Leu Glu Lys Ile Leu Gly Pro Val Ser Ser Gly
            420                 425                 430
His Val Glu Leu Arg Thr Thr Asp Pro Arg Ala Asn Pro Ser Val Thr
        435                 440                 445
Phe Asn Tyr Phe Arg Glu Ala Glu Asp Leu Glu Arg Cys Val His Gly
    450                 455                 460
Ile Glu Thr Ile Glu Arg Val Ile Gln Ser Arg Ala Phe Ser Asn Phe
465                 470                 475                 480
Thr Tyr Ala Asn Ala Ser Val Glu Ser Ile Phe Thr Asp Ser Ala Asn
                485                 490                 495
Phe Pro Val Asn Leu Leu Pro Arg His Val Asn Asp Ser Arg Ser Pro
            500                 505                 510
Glu Gln Tyr Cys Met Asp Thr Val Met Thr Ile Trp His Tyr His Gly
        515                 520                 525
Gly Cys His Val Gly Ala Val Val Asp Asp Tyr Arg Val Phe Gly
    530                 535                 540
Val Gln Gly Leu Arg Val Ile Asp Ser Ser Thr Phe Lys Tyr Ser Pro
545                 550                 555                 560
Gly Thr Asn Pro Gln Ala Thr Val Met Met Leu Gly Arg Tyr Met Gly
                565                 570                 575
Val Lys Ile Gln Ser Glu Arg Trp Lys Lys
```

580        585

<210> SEQ ID NO 8
<211> LENGTH: 1964
<212> TYPE: DNA
<213> ORGANISM: Sorghum vulgare

<400> SEQUENCE: 8

| | | | | | |
|---|---|---|---|---|---|
| atggcgcctg | ggcttgcgag | ctcggccgcg | ctgggggttt | tggccatcgt | tcttggctcc | 60 |
| tcgtgcctcg | tcgcgctctc | ggaggatggt | tcgtgccgtg | ccggactgca | tgccgtgaat | 120 |
| atggtcatgc | gttttttgttt | tcttttggat | tttctgcact | tctgcaaacg | tctgaatcgg | 180 |
| tgcatggtca | tatgtatgtg | cagagccact | ggagaacctg | cggttcgttc | gccacgcgca | 240 |
| ggacgcgccg | ctggtgtcgc | aatacaacta | catcgtcatc | ggcggcggca | cggcgggctg | 300 |
| cccgctggcg | gcgacgctgt | cggagcactc | ccgcgtgctg | ctcctggagc | gcggaggcct | 360 |
| cccctaccgc | aacatgtcca | accagcagca | cttcacggag | gcgctggcgg | acacgtcccc | 420 |
| ggcgtcgccc | gcgcagcggt | tcatctccga | ggacggcgtg | gtgaacgcgc | gggcgcgggt | 480 |
| gctgggcggc | gggagctgcc | tcaacgccgg | cttctacacg | cgggccagca | acgactacgt | 540 |
| gcgcgccgcc | gggtgggaca | cccgcctcgt | caactcctcg | taccactggg | tggagcgcgc | 600 |
| gctcgtgttc | cgcccggacg | tgccccatg | gcaggccgcg | ctccgcgacg | cgctgctgga | 660 |
| ggccggcgtc | acccccgaca | acggcttcac | cttcgaccac | gtcccgggca | ccaagatcgg | 720 |
| cggcaccatc | ttcgacagca | gcgggcagcg | gcacaccgcc | gccgacttcc | tccgccacgc | 780 |
| gcggcccagg | ggcctcaccg | tgttcctcta | cgctaccgtc | tcgaggatcc | tcttcaggca | 840 |
| gcaagagggc | gtgccgtacc | cggtggcgta | cggcgtggtg | ttcacggacc | cgctgggcgt | 900 |
| gcagcaccgg | gtgtacctcc | gcgacggcgg | caagaacgag | gtgatcctgt | ccgcggggac | 960 |
| gctggggagc | ccgcagctgc | tgatgctgag | cggcgtcgga | ccgcaggcgc | acctggaggc | 1020 |
| gcacggcatc | caggtgctgg | tcgaccagcc | catggtcggg | cagggcgtgg | ccgacaaccc | 1080 |
| catgaactcg | gtgttcatcc | cgtcgccggt | gcccgtcacg | ctctcgctcg | tgcaggtcgt | 1140 |
| cgggatcacc | cggttcggca | gcttcatcga | gggcgtcagc | ggctccgagt | tcggcatccc | 1200 |
| cgtctccgac | ggcgcccgcc | gcctagctcg | caacttcggc | ctcttctctc | ctcaggtgtg | 1260 |
| gtcggtcggt | ccggtcggtg | cttcgttcca | tactgacagc | aacatagccg | ccggaaatga | 1320 |
| aatgtactga | ctactgacgg | atcatcttgc | ggcagaccgg | gcagctgggc | acgctgccgc | 1380 |
| cgaagcagag | aaccccggag | gctctggagc | gggcggcgga | ggcgatgcgg | cggctggaca | 1440 |
| ggcgggcgtt | ccggggcggc | ttcatcctgg | agaagatcct | gggcccggtg | tcgtcgggc | 1500 |
| acatcgagct | gcggtccgcc | gacccgcgcg | cgaacccggc | ggtgacgttc | aactacttcc | 1560 |
| aggagtcgga | ggacctggag | cggtgcgtgc | acggcatcca | gacgatcgag | cgggtgatcc | 1620 |
| agtcccgggc | cttcgccaac | ttcacctacg | ccaacgcgtc | cgtggagtcc | atcttcaccg | 1680 |
| actccgccaa | cttccccgtc | aacctcctgc | gcgcggcacgt | caacgactcc | cggacgcccg | 1740 |
| agcagtactg | cagggacacc | gtcatgacca | tctggcacta | ccacggcgga | tgccaggtcg | 1800 |
| gcgccgtcgt | cgacgacgat | taccgggtgt | tcggcgtgca | gcggctcagg | gtgatcgaca | 1860 |
| gctccacgtt | caagtactcc | ccggggacca | acccgcaggc | caccgtcatg | atgctcggaa | 1920 |
| ggtatatggg | ggtgaaaatt | caggcccaga | gatggaggaa | atga | | 1964 |

<210> SEQ ID NO 9
<211> LENGTH: 582

<212> TYPE: PRT
<213> ORGANISM: Sorghum vulgare

<400> SEQUENCE: 9

```
Met Ala Pro Gly Leu Ala Ser Ser Ala Ala Leu Gly Val Leu Ala Ile
1               5                   10                  15

Val Leu Gly Ser Ser Cys Leu Val Ala Leu Ser Glu Asp Glu Pro Leu
            20                  25                  30

Glu Asn Leu Arg Phe Val Arg His Ala Gln Asp Ala Pro Leu Val Ser
        35                  40                  45

Gln Tyr Asn Tyr Ile Val Ile Gly Gly Gly Thr Ala Gly Cys Pro Leu
    50                  55                  60

Ala Ala Thr Leu Ser Glu His Ser Arg Val Leu Leu Leu Glu Arg Gly
65                  70                  75                  80

Gly Leu Pro Tyr Arg Asn Met Ser Asn Gln Gln His Phe Thr Glu Ala
                85                  90                  95

Leu Ala Asp Thr Ser Pro Ala Ser Pro Ala Gln Arg Phe Ile Ser Glu
            100                 105                 110

Asp Gly Val Val Asn Ala Arg Ala Arg Val Leu Gly Gly Gly Ser Cys
        115                 120                 125

Leu Asn Ala Gly Phe Tyr Thr Arg Ala Ser Asn Asp Tyr Val Arg Ala
130                 135                 140

Ala Gly Trp Asp Thr Arg Leu Val Asn Ser Ser Tyr His Trp Val Glu
145                 150                 155                 160

Arg Ala Leu Val Phe Arg Pro Asp Val Pro Pro Trp Gln Ala Ala Leu
                165                 170                 175

Arg Asp Ala Leu Leu Glu Ala Gly Val Thr Pro Asp Asn Gly Phe Thr
            180                 185                 190

Phe Asp His Val Pro Gly Thr Lys Ile Gly Gly Thr Ile Phe Asp Ser
        195                 200                 205

Ser Gly Gln Arg His Thr Ala Ala Asp Phe Leu Arg His Ala Arg Pro
    210                 215                 220

Arg Gly Leu Thr Val Phe Leu Tyr Ala Thr Val Ser Arg Ile Leu Phe
225                 230                 235                 240

Arg Gln Gln Glu Gly Val Pro Tyr Pro Val Ala Tyr Gly Val Val Phe
                245                 250                 255

Thr Asp Pro Leu Gly Val Gln His Arg Val Tyr Leu Arg Asp Gly Gly
            260                 265                 270

Lys Asn Glu Val Ile Leu Ser Ala Gly Thr Leu Gly Ser Pro Gln Leu
        275                 280                 285

Leu Met Leu Ser Gly Val Gly Pro Gln Ala His Leu Glu Ala His Gly
    290                 295                 300

Ile Gln Val Leu Val Asp Gln Pro Met Val Gly Gln Gly Val Ala Asp
305                 310                 315                 320

Asn Pro Met Asn Ser Val Phe Ile Pro Ser Pro Val Pro Val Thr Leu
                325                 330                 335

Ser Leu Val Gln Val Val Gly Ile Thr Arg Phe Gly Ser Phe Ile Glu
            340                 345                 350

Gly Val Ser Gly Ser Glu Phe Gly Ile Pro Val Ser Asp Gly Ala Arg
        355                 360                 365

Arg Leu Ala Arg Asn Phe Gly Leu Phe Ser Gln Thr Gly Gln Leu
    370                 375                 380

Gly Thr Leu Pro Pro Lys Gln Arg Thr Pro Glu Ala Leu Glu Arg Ala
385                 390                 395                 400
```

Ala Glu Ala Met Arg Arg Leu Asp Arg Arg Ala Phe Arg Gly Gly Phe
            405                 410                 415

Ile Leu Glu Lys Ile Leu Gly Pro Val Ser Ser Gly His Ile Glu Leu
            420                 425                 430

Arg Ser Ala Asp Pro Arg Ala Asn Pro Ala Val Thr Phe Asn Tyr Phe
            435                 440                 445

Gln Glu Ser Glu Asp Leu Glu Arg Cys Val His Gly Ile Gln Thr Ile
        450                 455                 460

Glu Arg Val Ile Gln Ser Arg Ala Phe Ala Asn Phe Thr Tyr Ala Asn
465                 470                 475                 480

Ala Ser Val Glu Ser Ile Phe Thr Asp Ser Ala Asn Phe Pro Val Asn
                485                 490                 495

Leu Leu Pro Arg His Val Asn Asp Ser Arg Thr Pro Glu Gln Tyr Cys
            500                 505                 510

Arg Asp Thr Val Met Thr Ile Trp His Tyr His Gly Gly Cys Gln Val
            515                 520                 525

Gly Ala Val Asp Asp Asp Tyr Arg Val Phe Gly Val Gln Arg Leu
        530                 535                 540

Arg Val Ile Asp Ser Ser Thr Phe Lys Tyr Ser Pro Gly Thr Asn Pro
545                 550                 555                 560

Gln Ala Thr Val Met Met Leu Gly Arg Tyr Met Gly Val Lys Ile Gln
                565                 570                 575

Ala Gln Arg Trp Arg Lys
            580

<210> SEQ ID NO 10
<211> LENGTH: 2870
<212> TYPE: DNA
<213> ORGANISM: Arabidopsis thaliana L.

<400> SEQUENCE: 10

```
accataggtc accaaagact ttataaataa cccatacatt atcatataca tataggcata      60
caaagtgaga gaactctact ctagattgtg ctaaactcaa tttgtattaa tgatggatag     120
attttggtca tggagattgt tgttgctct ctctcttttt ctccattctc caatttgttc     180
ttctgacaaa ggtaatattc atgaactaca actagattct taagtattca tattagtgcg     240
aagttatagt tttacccttt gatcgcagct ccgaactact ccttcatgcg ggacgcgaca     300
ggaagtccta caacgtcgta ctacgactat atcatcatcg gtggtgggac tgccgggtgc     360
cctctagccg caacgctgtc tcaaaacgcc agcgttttgc tgctcgaacg cggtgactca     420
ccgtacaata accccaacat cacgaggctc tcggctttcg gagccgctct ctctgacctg     480
tctgagtcct caccatctca gcgttttgta tcagaagatg gtgtcattaa tgcacgtgct     540
cgggttctcg gtggcggaag cgctctcaac gccggcttct atacacgtgc gggcactaaa     600
tacgttaggt tagtgcatat gtatacagta acactaatac gcatgcatac aatttacatg     660
gaaattaata tattatcgag tcctcattct tactatggtt ggtgagacag taataattgt     720
agacattatt atatgatcaa tcaactaagg tctaaggata acattaaata tatgtataac     780
tatatattat cacacacact taataaaaga gaaacgatt tttgccgtaa aaataaaaat     840
aaaagagaaa acgatcttat tatacttata tgtagaatag tcatttaatc tgttagggtc     900
gttacatagt acaacataca agatatttct tattgttgat gttttttggtg acttggtgtg     960
tccacgttaa aataaataat ttatacgaat cgaaatgttg ttaggaacat gggttgggac    1020
```

```
ggagcgctag cgaacgagtc gtaccagtgg gttgaagcta aggtggcgtt tcagcctccg    1080
atggggcggt ggcaaacggc cgtgagagac ggcttattgg aggctgggat tgtccctaat    1140
aatggtttca cctatgatca tatcaatggc accaaatttg gcggtactat ttttgaccgc    1200
aacggcaata gacacaccgc cgccgatttg ttagagtatg ccgatcctaa gggtattacc    1260
gtccttttgc atgccaccgt ccaccggatc ttgtttcgta ctcgaggtac ttaatgtagc    1320
attgcagaat ataatcatcc aatactcata acgtagtaaa actaaaatat attcaatcat    1380
gctggttaaa caaaaatgtt ggtcctgttt tcacatggtt aaatttttt catcttaata    1440
tggattgaac ctgatatttt gcaaaatcaa tgtctacctt tttttcacta tacatttcat    1500
gtaaattctt gcttaccaca ctttattcta attcattttg ttgccactaa atcagattat    1560
taactaacta tcaaattacc aatataatta ttcacgttta aggtacgacc aagccaatag    1620
ccaacggagt tgtgtaccga gaccggaccg gtcaggctca tagagcttac ctaaaggaag    1680
gcgccttgag tgagatcatc ctatcggccg gaacccctagg gagcccacaa cttcttatgc    1740
taagtggtgt tggcccatcg gctcaattac aggcccaaaa catcacggtg gtgatggacc    1800
agcctcatgt gggtcaaggc atgtatgaca accctatgaa tgccgtgttc gttccttctc    1860
cagtccccgt tgaggtctca ctcattgagg ttgttgggat taccggggaa ggaacatatg    1920
tcgaagccgc cggtggtgaa aattttggcg gaggtggtgg tggttctagt ggatcgtcct    1980
ccactagaga ctactatgca atgttttcac caagggcaac attattagag tcaaattcaa    2040
tgaccaaatt atcatcagcc caaccttttc aaggaggctt ccttttagag aaagtaatgg    2100
gcccattatc aacgggtcat ttagagctca agacccgaaa cccaaaagat aacccgattg    2160
tgactttcaa ctatttccaa catcctgacg acctaaaacg ttgtgttcga ggaatccaaa    2220
ccatagagag agtcgtgcaa tctaaagctt tttcgaggta taagtacgca gatgtgtcat    2280
ttgagtattt acttaacctc acggcgagta ctcctgtcaa tctaaggccg cctcgcagtg    2340
gtcctggagc ctcgttgcct ccatccgcag aggaattttg ccaacataca gttacaacca    2400
tttggcatta ccatggagga tgcgttgtgg gcagagtggt cgatggggat tataaagtta    2460
ttggtatcga ccggcttaga gtcattgata tgtcgaccgt tggttattgt cccgggacaa    2520
atcctcaagc cacggttatg atgcttggca ggtaaaatca atcatatata ttaattatgt    2580
tgatgttttt tgtttttttt tactaaaggc taatgatttt ggcaggtata tgggtgtgaa    2640
gatcttgaga gagagactca ccaagaagta gggttttgaa tcggatcagg ggttttggga    2700
aaacgttata ttaaaaatga aatgaatcaa gatattacta atcgatgtta ttaatagctg    2760
aatatgtatt gttcttggta atttctgttt ggtacttatt attagaccaa actgagatgt    2820
atacggaaat atatgtatag actcattccc aattttcaaa actctgttcc                2870
```

<210> SEQ ID NO 11
<211> LENGTH: 572
<212> TYPE: PRT
<213> ORGANISM: Arabidopsis thaliana L.

<400> SEQUENCE: 11

Met Met Asp Arg Phe Trp Ser Trp Arg Leu Phe Val Ala Leu Ser Leu
1               5                   10                  15

Phe Leu His Ser Pro Ile Cys Ser Ser Asp Lys Ala Pro Asn Tyr Ser
                20                  25                  30

Phe Met Arg Asp Ala Thr Gly Ser Pro Thr Thr Ser Tyr Tyr Asp Tyr
            35                  40                  45

```
Ile Ile Ile Gly Gly Gly Thr Ala Gly Cys Pro Leu Ala Ala Thr Leu
 50                  55                  60

Ser Gln Asn Ala Ser Val Leu Leu Glu Arg Gly Asp Ser Pro Tyr
 65                  70                  75                  80

Asn Asn Pro Asn Ile Thr Arg Leu Ser Ala Phe Gly Ala Ala Leu Ser
                 85                  90                  95

Asp Leu Ser Glu Ser Ser Pro Ser Gln Arg Phe Val Ser Glu Asp Gly
            100                 105                 110

Val Ile Asn Ala Arg Ala Arg Val Leu Gly Gly Ser Ala Leu Asn
            115                 120                 125

Ala Gly Phe Tyr Thr Arg Ala Gly Thr Lys Tyr Val Arg Asn Met Gly
    130                 135                 140

Trp Asp Gly Ala Leu Ala Asn Glu Ser Tyr Gln Trp Val Glu Ala Lys
145                 150                 155                 160

Val Ala Phe Gln Pro Pro Met Gly Arg Trp Gln Thr Ala Val Arg Asp
                165                 170                 175

Gly Leu Leu Glu Ala Gly Ile Val Pro Asn Asn Gly Phe Thr Tyr Asp
            180                 185                 190

His Ile Asn Gly Thr Lys Phe Gly Gly Thr Ile Phe Asp Arg Asn Gly
            195                 200                 205

Asn Arg His Thr Ala Ala Asp Leu Leu Glu Tyr Ala Asp Pro Lys Gly
    210                 215                 220

Ile Thr Val Leu Leu His Ala Thr Val His Arg Ile Leu Phe Arg Thr
225                 230                 235                 240

Arg Gly Thr Thr Lys Pro Ile Ala Asn Gly Val Val Tyr Arg Asp Arg
                245                 250                 255

Thr Gly Gln Ala His Arg Ala Tyr Leu Lys Glu Gly Ala Leu Ser Glu
            260                 265                 270

Ile Ile Leu Ser Ala Gly Thr Leu Gly Ser Pro Gln Leu Leu Met Leu
            275                 280                 285

Ser Gly Val Gly Pro Ser Ala Gln Leu Gln Ala Gln Asn Ile Thr Val
    290                 295                 300

Val Met Asp Gln Pro His Val Gly Gln Gly Met Tyr Asp Asn Pro Met
305                 310                 315                 320

Asn Ala Val Phe Val Pro Ser Pro Val Pro Val Glu Val Ser Leu Ile
                325                 330                 335

Glu Val Val Gly Ile Thr Gly Glu Gly Thr Tyr Val Glu Ala Ala Gly
            340                 345                 350

Gly Glu Asn Phe Gly Gly Gly Gly Gly Ser Ser Gly Ser Ser Ser
            355                 360                 365

Thr Arg Asp Tyr Tyr Ala Met Phe Ser Pro Arg Ala Thr Leu Leu Glu
    370                 375                 380

Ser Asn Ser Met Thr Lys Leu Ser Ser Ala Gln Pro Phe Gln Gly Gly
385                 390                 395                 400

Phe Leu Leu Glu Lys Val Met Gly Pro Leu Ser Thr Gly His Leu Glu
                405                 410                 415

Leu Lys Thr Arg Asn Pro Lys Asp Asn Pro Ile Val Thr Phe Asn Tyr
            420                 425                 430

Phe Gln His Pro Asp Asp Leu Lys Arg Cys Val Arg Gly Ile Gln Thr
            435                 440                 445

Ile Glu Arg Val Val Gln Ser Lys Ala Phe Ser Arg Tyr Lys Tyr Ala
    450                 455                 460

Asp Val Ser Phe Glu Tyr Leu Leu Asn Leu Thr Ala Ser Thr Pro Val
```

```
                        465                 470                 475                 480
Asn Leu Arg Pro Pro Arg Ser Gly Pro Gly Ala Ser Leu Pro Pro Ser
                    485                 490                 495
Ala Glu Glu Phe Cys Gln His Thr Val Thr Thr Ile Trp His Tyr His
                500                 505                 510
Gly Gly Cys Val Val Gly Arg Val Asp Gly Asp Tyr Lys Val Ile
            515                 520                 525
Gly Ile Asp Arg Leu Arg Val Ile Asp Met Ser Thr Val Gly Tyr Cys
        530                 535                 540
Pro Gly Thr Asn Pro Gln Ala Thr Val Met Met Leu Gly Arg Tyr Met
545                 550                 555                 560
Gly Val Lys Ile Leu Arg Glu Arg Leu Thr Lys Lys
                565                 570

<210> SEQ ID NO 12
<211> LENGTH: 678
<212> TYPE: DNA
<213> ORGANISM: artificial sequence
<220> FEATURE:
<223> OTHER INFORMATION: the open reading frame of RFP(r) gene

<400> SEQUENCE: 12
atggcctcct ccgagaacgt gatcaccgag ttcatgcgct tcaaggtgcg catggagggc      60
accgtgaacg gccacgagtt cgagatcgag ggcgagggcg agggccgccc ctacgagggc     120
cacaacaccg tgaagctgaa ggtgaccaag gcggcccccc tgcccttcgc ctgggacatc     180
ctgtcccccc agttccagta cggctccaag gtgtacgtga agcaccccgc cgacatcccc     240
gactacaaga agctgtcctt ccccgagggc ttcaagtggg agcgcgtgat gaacttcgag     300
gacggcggcg tggccaccgt gacccaggac tcctccctgc aggacggctg cttcatctac     360
aaggtgaagt tcatcggcgt gaacttcccc tccgacggcc ccgtgatgca gaagaagacc     420
atgggctggg aggcctccac cgagcgcctg taccccgcg acggcgtgct gaagggcgag     480
acccacaagg ccctgaagct gaaggacggc ggccactacc tggtggagtt caagtccatc     540
tacatggcca agaagcccgt gcagctgccc ggctactact acgtggacgc caagctggac     600
atcacctccc acaacgagga ctacaccatc gtggagcagt acgagcgcac cgagggccgc     660
caccacctgt cctgtag                                                    678

<210> SEQ ID NO 13
<211> LENGTH: 812
<212> TYPE: DNA
<213> ORGANISM: Hordeum vulgare L.

<400> SEQUENCE: 13
aaccgtctct tcgtgagaat aaccgtggcc taaaaataag ccgatgagga taaataaaat      60
gtggtggtac agtacttcaa gaggtttact catcaagagg atgcttttcc gatgagctct     120
agtagtacat cggacctcac atacctccat tgtggtgaaa tattttgtgc tcatttagtg     180
atgggtaaat tttgtttatg tcactctagg ttttgacatt tcagttttgc cactcttagg     240
ttttgacaaa taatttccat tccgcggcaa aagcaaaaca attttatttt acttttacca     300
ctcttagctt tcacaatgta tcacaaatgc cactctagaa attctgttta tgccacagaa     360
tgtgaaaaaa aacactcact tatttgaagc caaggtgttc atggcatgga aatgtgacat     420
aaagtaacgt tcgtgtataa gaaaaaattg tactcctcgt aacaagagac ggaaacatca     480
tgagacaatc gcgtttggaa ggctttgcat caccctttgga tgatgcgcat gaatggagtc     540
```

```
gtctgcttgc tagccttcgc ctaccgccca ctgagtccgg gcggcaacta ccatcggcga    600
acgacccagc tgacctctac cgaccggact tgaatgcgct accttcgtca gcgacgatgg    660
ccgcgtacgc tggcgacgtg ccccgcatg catggcggca catggcgagc tcagaccgtg     720
cgtggctggc tacaaatacg taccccgtga gtgccctagc tagaaactta cacctgcaac    780
tgcgagagcg agcgtgtgag tgtagccgag ta                                  812

<210> SEQ ID NO 14
<211> LENGTH: 349
<212> TYPE: DNA
<213> ORGANISM: Solanum tuberosum L.

<400> SEQUENCE: 14
ttcgaacgcg taggtaccac atggttaacc tagacttgtc catcttctgg attggccaac     60
ttaattaatg tatgaaataa aaggatgcac acatagtgac atgctaatca ctataatgtg    120
ggcatcaaag ttgtgtgtta tgtgtaatta ctagttatct gaataaaaga gaaagagatc    180
atccatattt cttatcctaa atgaatgtca cgtgtcttta taattctttg atgaaccaga    240
tgcatttcat taaccaaatc catatacata taaatattaa tcatatataa ttaatatcaa    300
ttgggttagc aaaacaaatc tagtctaggt gtgttttgcg aatgcggcc               349

<210> SEQ ID NO 15
<211> LENGTH: 1922
<212> TYPE: DNA
<213> ORGANISM: Zea mays L.

<400> SEQUENCE: 15
atggcgcctg ggcttgcgaa ctgggtcgcg ctggttctga ccgtcctcct tggtctctcg     60
tgcctcgtcg tcgcgctctc ggaggatggt ttgtgccgga cttgtcacgc gctctttggt    120
atttctgcag ttctgcaaac gtgtgaattg catggacat gtgcagaaac actggacaag     180
ctgcggttcg tgcgccacgc acaggacgcg cccctggtgt cgcagtacaa ctacatcgtg    240
atcggcggcg gcacggcggg gtgcccgctg gcggcgacgc tgtcggagca ctcgcgcgtg    300
ctgctcctgg agcgcggggg cctcccgtcc cgcaacatgt ccgaccagca gcacttcacg    360
gacgcgctgg cggacacgtc cccggcgtcg cccgcgcagc ggttcgtgtc cgaggacggc    420
gtggtgaacg cgcggggcccg ggtgctgggc ggggcagct gcctcaacgc cgggttctac    480
acgcgggcca gcaccgacta cgtgcgcgcc gccggctggg acgcccgcct cgtcaactcg    540
tcctaccgct gggtggagcg cgcgctcgtg ttccgccccg ccgtgccccc gtggcaggcc    600
gcgctccgcg acgcgctgct cgaggccggc gtcacgcccg acaacggctt caccttcgac    660
cacgtcacgg gcaccaagat cggggggcacc atcttcgaca gcagcggcca gcgccacacc    720
gccgccgact tcctccgcca cgcgcgcccc aggggggctca ccgtgttcct ctacgctacc    780
gtctccagga tcctcttcag acagcaaggt acgtacgtgc gtgcacggct tccgcatttt    840 ttttcgaca gtgcgggctg gcacgatcgc gctctgaagc ggagaatcgt gcgctgtcga    900
cagagggcgt gccgtacccg gtggcgtacg gtgtggtgtt cacggacccg ctcggggtgc    960
agcaccgggt gtacctccgg gacggcgcca agaacgaggt gatcctgtcg gcgggggacgc   1020 tggggagccc gcagctgctg atgctgagcg gcgtcggccc gcaggcgcac ctggaggcgc   1080
acggcgtcca ggtgctggtg gaccagccca tggtcgggca gggcgtggct gacaacccga   1140
tgaactcggt gttcatcccg tcgccggtgc ccgtcacgct gtcgctcgtg caggtcgtcg   1200
```

```
ggatcacccg gtccggcagc ttcatcgagg gcgtgagcgg ctccgagttc ggcatccccg    1260
tctccgaggg cgcccgtcgc ctggctcgca gcttcggcct cttctctccg cagacggggc    1320
agctgggcac gttgccgccg aagcagagaa ccccagaggc cctggagcgc gcggcggagg    1380
cgatgcggcg gctggacagg cgggcgttcc ggggcggatt catcctggag aagatcctgg    1440
gccccgtctc ctcgggccac gtcgagctgc ggtccgccga cccgcgcgcg aacccggcgg    1500
tgacgttcaa ctacttccag gagtcggagg acctgcagcg gtgcgtgcgc ggcatccaga    1560
cgatcgagcg cgtgatccag tcccgggcct tcgccaactt cacctacgcc aacgcttcca    1620
cggagtccat cttcaccgac tccgccaact tccccgtcaa cctcctgccg cggcacgtca    1680
acgactcccg gacgcccgag cagtactgca gggacaccgt catgaccatc tggcattacc    1740
acggcgggtg ccaggtcggc gccgtcgtgg acgacgatta ccgggtgttc ggcgtgcagc    1800
gactgagggt gatcgacagc tccacgttca agtactcccc cggcaccaac ccgcaggcca    1860
ccgtcatgat gctcggaagg tatatgggtg tgaaaattca ggccgagaga tggaggaaat    1920
ga                                                                   1922

<210> SEQ ID NO 16
<211> LENGTH: 388
<212> TYPE: DNA
<213> ORGANISM: Zea mays L.

<400> SEQUENCE: 16
tcgagatttc aagtttcagc atggtctagg gactaggcct ctagctgtga taatgaatat      60
caatcaacac atctgtaact gggtaactgc tctagcctct agagtaggtt ttatttttct     120
ctagatattt ttttaatctc ctctagacat actcctagct tccgcatgtt gttggttcca     180
tttcaccaca cccctagatg cattgttcag catttcgcgg gaataatgag aattatgctg     240
aaaaggcatg atcgctcctc ctgcctattc tacagaaaat taaataaaga accgccattt     300
catcaaataa accaaaggcc gtgttctgtg gattggaagg gatcgaggaa gattaaatcg     360
tttctattta attttccctt aatttttaa                                       388

<210> SEQ ID NO 17
<211> LENGTH: 1488
<212> TYPE: DNA
<213> ORGANISM: Zea mays L.

<400> SEQUENCE: 17
atggcggcga caatggcagt gacgacgatg gtgacgagga gcaaggagag ctggtcgtca      60
ttgcaggtcc cggcggtggc attcccttgg aagccacgag gtggcaagac cggcggcctc     120
gagttccctc gccgggcgat gttcgccagc gtcggcctca acgtgtgccc gggcgtcccg     180
gcggggcgcg acccgcggga gcccgatccc aaggtcgtcc gggcggcctg cggcctggtc     240
caggcacaag tcctcttcca ggggtttaac tgggagtcgt gcaagcagca gggaggctgg     300
tacaacaggc tcaaggccca ggtcgacgac atcgccaagg ccggcgtcac gcacgtctgg     360
ctgcctccac cctcgcactc cgtctcgcca caaggctaca tgccaggccg cctatacgac     420
ctggacgcgt ccaagtacgg cacggcggcg gagctcaagt ccctgatagc ggcgttccac     480 ggcagggggcg tgcagtgcgt ggcggacatc gtcatcaacc accggtgcgc ggaaaagaag     540
gacgcgcgcg gcgtgtactg catcttcgag ggcgggactc ccgacgaccg cctggactgg     600
ggccccggga tgatctgcag cgacgacacg cagtactcgg acgggacggg gcaccgcgac     660
acgggcgagg ggttcgcggc ggcgcccgac atcgaccacc tcaacccgcg cgtgcagcgg     720
```

```
gagctctccg cctggctcaa ctggctcagg tccgacgccg tggggttcga cggctggcgc      780
ctcgacttcg ccaagggcta ctcgccggcc gtcgccagaa tgtacgtgga gagcacgggg      840
ccgccgagct tcgtcgtcgc ggagatatgg aactcgctga gctacagcgg ggacggcaag      900
ccggcgccca accaggacca gtgccggcag gagctgctgg actggacgcg ggccgtcggc      960
gggcccgcca tggcgttcga cttccccacc aagggcctgc tgcaggcggg cgtgcagggg     1020
gagctgtggc ggctgcgcga cagctccggc aacgcggccg gcctgatcgg gtgggcgccc     1080
gagaaggccg tcaccttcgt cgacaaccat gacaccgggt cgacgcagaa gctctggccg     1140
ttcccatccg acaaggtcat gcagggctac gcctacatcc tcacccatcc aggagtcccc     1200
tgcattttct acgaccacat gttcgactgg aacctgaagc aggagatatc cacgctgtct     1260
gccatcaggg cgcggaacgg catccgcgcc gggagcaagc tgcggatcct cgtggcggac     1320
gcggacgcgt acgtggccgt cgtcgacgag aaggtcatgg tgaagatcgg gacaaggtac     1380
ggcgtgagca gcgtggtccc gtcggatttc caccccggcg gcgcacggcaa ggactactgc     1440 gtctgggaga agcgagcct ccgcgtcccg gcggggcgcc acctctag                    1488
```

<210> SEQ ID NO 18
<211> LENGTH: 2737
<212> TYPE: DNA
<213> ORGANISM: Zea mays L.

<400> SEQUENCE: 18

```
tgcaccggac actgtctggt ggcataccag acagtccggt gtgccagatc agggcaccct       60
tcggttcctt tgctcctttg cttttgaacc ctaactttga tcgtttattg gtttgtgttg      120
aacctttatg cacctgtgga atatataatc tagaacaaac tagttagtcc aatcatttgt      180
gttgggcatt caaccaccaa aattatttat aggaaaaggt taaaccttat ttcccttca      240 atctcccct ttttggtgat tgatgccaac acaaaccaaa gaaatatat aagtgcagaa      300 ttgaactagt ttgcataagg taagtgcata ggttacttag aattaaatca atttatactt     360
ttacttgata tgcatggttg ctttcttta ttttaacatt ttggaccaca tttgcaccac       420
ttgttttgtt ttttgcaaat cttttttggaa attcttttc aaagtctttt gcaaatagtc     480
aaaggtatat gaataagatt gtaagaagca ttttcaagat ttgaaatttc tccccctgtt     540
tcaaatgctt ttcctttgac taaacaaaac tcccctgaa taaaattctc tcttagctt       600 tcaagagggt tttaaataga tatcaattgg aaatatattt agatgctaat tttgaaaata     660
taccaattga aaatcaacat accaatttga aattaaacat accaatttaa aaatttcaa     720 aaagtggtgg tgcggtcctt ttgctttggg cttaatattt ctccccctt ggcattaatc     780 gccaaaaacg gagactttgt gagccattta tactttctcc ccattggtaa atgaaatatg     840
agtgaaagat tataccaaat ttggacagtg atgcggagtg acggcgaagg ataaacgata     900
ccgttagagt ggagtggaag ccttgtcttc gccgaagact ccatttccct ttcaatctac     960
gacttagcat agaaatacac ttgaaaacac attagtcgta gccacgaaag agatatgatc    1020
aaaggtatac aaatgagcta tgtgtgtaat gtttcaatca agtttcgag aatcaagaat     1080 atttagctca ttcctaagtt tgctaaaggt tttatcatct aatggtttgg taagatatc      1140 gactaattgt tctttggtgc taacataagc aatctcgata tcacccctt gttggtgatc     1200 cctcaaaaag tgataccgaa tgtctatgtg cttagtgcgg ctgtgttcaa cgggattatc    1260
cgccatgcag atagcactct cattgtcaca taggagaggg actttgctca atttgtagcc   1320
```

```
atagtccata aggttttgcc tcatccaaag taattgcaca caacaatgtc ctgcggcaat    1380
atacttggct tcggcggtag aaagagctat tgagttttgt ttctttgaag tccaagacac    1440
cagggatctc cctagaaact gacaagtccc tgatgtgctc ttcctatcaa ttttacaccc    1500
tgcccaatcg gcatctgaat atcctattaa atcaaaggtg gatcccttgg ggtaccaaag    1560
accaaattta ggagtgtaaa ctaaatatct catgattctt ttcacggccc taaggtgaac    1620
ttccttagga tcggcttgga atcttgcaca catgcatata gaaagcatac tatctggtcg    1680
agatgcacat aaatagagta aagatcctat catcgaccgg tataccttt  ggtctacgga    1740 tttacctccc gtgtcgaggt cgagatgccc attagttccc atgggtgtcc tgatgggctt    1800
ggcatccttc attccaaact tgttgagtat gtcttgaatg tactttgttt ggctgatgaa    1860
ggtgccatct tggagttgct tgacttgaaa tcctagaaaa tatttcaact tccccatcat    1920
agacatctcg aatttcggaa tcatgatcct actaaactct tcacaagtag atttgttagt    1980
agacccaaat ataatatcat caacataaat ttggcataca aacaaaactt ttgaaatggt    2040
tttagtaaag agagtaggat cggctttact gactctgaag ccattagtga taagaaaatc    2100
tcttaggcat tcataccatg ctgttggggc ttgcttgagc ccataaagcg cctttgagag    2160
tttataaaca tggttagggt actcactatc ttcaaagccg agaggttgct caacatagac    2220
ctattcaccc catttgatca cttttttggt ccttcaggat ctaatagtta tgtataattt    2280
agagtctctt gtttaatggc cagatatttc taattaatct aagaatttat gatatttttt    2340 aatttttat  catgtctgat gagaattaac ataaaggctc aattgggtcc tgaattaata    2400
atagagtgaa aattaatcca gaggctctat tagaaccttc aattagtaat accaagatat    2460
atataagata gtagagtata gtttaaatgt tggcattgtt cattcttct tttgttattt    2520 aatttatgct ttccacggtg gttagtggtt acttctgaag ggtccaaata atgcatgaag    2580
agtttgagga caagaagtct gccctaaaaa tagcgatgca aaggcatggt gtccaagcca    2640
tacatatagc gcactaattt tatcagcaga acaatggtat ttataggtcc tagtgcccag    2700
gcaacaagag acacgaataa agcatcgatc acgacac                             2737
```

```
<210> SEQ ID NO 19
<211> LENGTH: 225
<212> TYPE: DNA
<213> ORGANISM: Zea mays L.

<400> SEQUENCE: 19
atggcggcga caatggcagt gacgacgatg gtgacgagga gcaaggagag ctggtcgtca     60
ttgcaggtcc cggcggtggc attcccttgg aagccacgag gtggcaagac cggcggcctc    120
gagttccctc gccgggcgat gttcgccagc gtcggcctca acgtgtgccc gggcgtcccg    180
gcggggcgcg acccgcggga gcccgatccc aaggtcgtcc gggcg                    225

<210> SEQ ID NO 20
<211> LENGTH: 348
<212> TYPE: DNA
<213> ORGANISM: Zea mays L.

<400> SEQUENCE: 20
gatctgacaa agcagcatta gtccgttgat cggtggaaga ccactcgtca gtgttgagtt     60
gaatgtttga tcaataaaat acggcaatgc tgtaagggtt gttttttatg ccattgataa    120
tacactgtac tgttcagttg ttgaactcta tttcttagcc atgccaagtg cttttcttat    180
tttgaataac attacagcaa aaagttgaaa gacaaaaaaa aaaaccccg  aacagagtgc    240
```

```
tttgggtccc aagctacttt agactgtgtt cggcgttccc cctaaatttc tccccctata      300
tctcactcac ttgtcacatc agcgttctct ttccccatata tctccacg                  348
```

USE OF GENIC MALE STERILITY GENE AND MUTATION THEREOF IN HYBRIDIZATION

TECHNICAL FIELD

The present invention belongs to the field of biotechnology, and particularly describes a hybrid breeding method for crops, which comprises sterile line reproduction and hybrid seed production, and it more particularly describes maize ZmFL1 gene or alleles thereof, as well as mutant plants due to changes in the gene.

BACKGROUND

Maize is a major food crop in China, and plays an important role in feeding and bioenergy, and now has become the crop with the largest planting area and the highest total yield in China. Heterosis is widely used to substantially improve yield, resistance, and quality of crops. Maize is among the crops of which heterosis has long been utilized. The first maize hybrid emerged in 1924. The main bottleneck for utilizing heterosis of maize is emasculation of the female parent for seed production. There are mainly two modes of emasculation employed in commercial breeding: manual emasculation and mechanical emasculation. However, there are disadvantages for both of the two emasculation modes: manual emasculation is incomplete, subject to the decrease of seed purity, and meanwhile greatly increases the cost, while mechanical emasculation requires specific plant architecutre with sparse upper leaves and large and flat planting plots. However, the maize varieties in China predominantly have compact architecture. In addition, mechanical emasculation is unfeasible in the northwest of China such as Gansu Province, mainly due to the fragmentation of the seed production areas. Meanwhile, in maize hybrid seed production, there exists the problem that the genetic backgrounds of the parental lines commonly used for breeding are not substantially different, and therefore affects the fulfillment of the main breeding objectives such as high yield, stable yield, resistance, early maturity, etc. Male sterility can be used in seed production not only to avoid the problem of seed purity decrease due to the incomplete emasculation of the female parent, but also to replace mechanical emasculation and reduce seed production costs; and the most fundamental step for this technology to be used in seed production lies in obtaining sterile lines with complete and stable sterility and the corresponding restorer lines that can be easily found. Maize cytoplasmic male sterility line is susceptible to leaf spot disease and it is hard to obtain the corresponding restorer line, but the nuclear male sterile line could overcome leaf spot disease and the corresponding restorer line can be easily found. Therefore, it is important to strengthen the research on the maize nuclear male sterile mutants and the controlling genes in hybrid breeding and production of maize.

To solve the problems in the current method for maize hybrid breeding, such as the technology bottlenecks including incomplete manual emasculation, the limited variety resources for hybrid breeding, the complexity in seed production technology, and the high cost of seed production and so on; people are trying a new hybrid breeding technology, in which the new hybrid breeding technology fully utilizes male sterile genes controlled by recessive nuclear genes to construct sterile lines with stable fertility that is not affected by environment. The main technical advantages include: firstly, the step of either manual emasculation or mechanical emasculation is omitted, seeds with higher quality and purity can be supplied to the growers; secondly, the recessive nuclear sterile genes used are applicable to the great majority of varieties, which greatly improves the utilization of the heterosis resources and solves the problem for the utilization of the heterosis resources; thirdly, sterile line reproduction via hybridization is simplified. The present invention provides a maize gene involved in pollen development and a male sterile line produced based on the mutation of the gene, which has stable fertility and is not generally affected by environmental conditions. This gene and the sterile line produced based on the mutation of the gene provide essential elements for constructing a novel hybrid breeding system.

SUMMARY

All references mentioned herein are incorporated herein by reference.

Unless otherwise specified, all technical and scientific terms used herein have the same meanings as commonly understood by one of ordinary skill in the art to which the present invention pertains. Unless otherwise specified, the techniques used or mentioned herein are standard techniques well known by one of ordinary skill in the art. Materials, methods and examples are used merely for illustration, not for limitation.

The present invention includes a fertility-related gene and nucleotide and protein sequences thereof, and further includes the application in regulating the male fertility of plants by means of manipulation of the gene. By way of non-limiting examples, any methods described hereinafter can be used in connection with the corresponding nucleotide sequences provided by the present invention; for example, the mutant version of the fertility gene is introduced into plants to cause the male sterility of the plants, to mutate the endogenous sequence of the plants, to introduce an antisense sequence of the gene sequence into the plants, to use a hairpin form, or to ligate the sequence to other nucleotide sequences to regulate the phenotypes of the plants, or any one method of multiple methods known to a person in the art, which can be used to influence the male fertility of the plants.

The present invention provides a male sterility restorer gene and a male sterility mutant material of the gene, and the use of the gene and the mutant material thereof in breeding.

In the first aspect of the present invention, the present invention provides a fertility restorer gene FL1, the nucleotide sequence thereof being selected from one sequence of the following group:

(a) the nucleotide sequence shown in SEQ ID NO:1 or SEQ ID NO:2;
(b) the nucleotide sequence shown in SEQ ID NO:6;
(c) the nucleotide sequence shown in SEQ ID NO:8;
(d) the nucleotide sequence shown in SEQ ID NO:10;
(e) a DNA sequence capable of hybridizing with DNA of any one sequence of (a)-(d) under stringent conditions;
(f) a DNA sequence which is complementary to any one sequence of (a)-(d).

wherein maize ZmFL1 gene has the nucleotide sequence as shown in SEQ ID NO:1 or 2, the encoded amino acid sequence thereof being as shown in SEQ ID NO:3; rice OsFL1 gene has the nucleotide sequence as shown in SEQ ID NO:6, the encoded amino acid sequence thereof being as shown in SEQ ID NO: 7; sorghum SvFL1 gene has the nucleotide sequence as shown in SEQ ID NO:8, the encoded amino acid sequence thereof being as shown in SEQ ID NO:9; and *Arabidopsis thaliana* AtFL1 gene has the nucleotide sequence as shown in SEQ ID NO:10, the encoded amino acid sequence thereof being as shown in SEQ ID NO:11.

A person skilled in the art should be aware that the fertility restorer gene FL1 described in the present invention also comprises a highly-homologous and functionally equivalent sequence, which shows high homology to nucleotide sequences SEQ ID NO:1, 2, 6, 8 or 10 and has the same fertility-regulation function. The highly-homologous and functionally equivalent sequence comprises a DNA sequence hybridizable with a DNA of the sequence shown in SEQ ID NO:1, 2, 6, 8 or 10 under stringent conditions. The "stringent conditions" used herein are well known, and include, for example, hybridizing in a hybridization solution containing 400 mM NaCl, 40 mM PIPES (pH 6.4) and 1 mM EDTA at 60° C. for 12-16 h, and then washing with a washing solution containing 0.1% SDS and 0.1% SSC at 65° C. for 15-60 min.

The functionally equivalent sequence also includes a DNA sequence with at least 90%, 95%, 96%, 97%, 98%, or 99% sequence identity to the sequence shown in SEQ ID NO:1, 2, 6, 8 or 10 and having fertility-regulating function, which can be obtained from any plants. Wherein percentage of sequence identity can be obtained by well-known bioinformatics algorithms, including Myers and Miller algorithm (Bioinformatics, 4(1):11-17, 1988), Needleman-Wunsch global alignment (J. Mol. Biol., 48(3): 443-53, 1970), Smith-Waterman local alignment (J. Mol. Biol., 147: 195-197, 1981), Pearson-Lipman similarity search method (PNAS, 85(8): 2444-2448, 1988), and Karlin and Altschul statistics (Altschul et al., J. Mol. Biol., 215(3): 403-410, 1990; PNAS, 90: 5873-5877, 1993). This is familiar to a person skilled in the art.

In a second aspect of the present invention, the present invention also provides an expression cassette, which contains a DNA sequence of the fertility restorer gene disclosed in the present invention, being selected from the following sequences:

(a) the sequence shown in SEQ ID NO:1, 2, 6, 8 or 10;

(b) a DNA sequence being hybridizable with a DNA of a sequence of (a) under stringent conditions;

(c) a DNA sequence with at least 90% (preferably at least 95%) sequence identity to the sequence of (a) and with the same function; and (d) a DNA sequence complementary to any one sequence of (a)-(c).

In the third aspect of present invention, the present invention also provides a male sterile plant mutant, and the male sterile mutant loses male fertility due to mutations in the plant endogenous gene of SEQ ID NO:1, 2, 6, 8 or 10, or mutations in the nucleotides of a gene highly homologous thereto. The "mutations" include, but not limited to, the following, such as gene mutations caused by a physical or chemical method, the chemical method including mutagenesis by a mutagen treatment using a mutagen such as EMS and the like, in which the mutation can be a point mutation, can be a DNA deletion or an insertion mutation, and gene mutations produced by a method such as gene silencing by RNAi or site-directed gene mutagenesis, the method of site-directed gene mutagenesis includes, but not limited to, ZFN site-directed gene mutagenesis method, TALEN site-directed gene mutagenesis method, and/or CRISPR/Cas9 site-directed gene mutagenesis method, etc.

In particular, the maize male sterile mutant zmfl1 provided in the present invention contains a mutated male sterile gene caused by insertion of Mutator transposon; the mutations of the gene caused by insertion of two Mutator transposons are respectively found in the maize fertility gene ZmFL1 in the present invention, each of them causing the male sterile phenotype of maize, in which the Mutator insertion sites are chr1: 80,964,768 (MU1) and chr1: 80,963,850 (MU3), respectively; and the premature termination of gene expression has resulted from the Mutator insertion, thus failing to encode a functional protein.

In the fourth aspect of the present invention, the present invention also provides a promoter pZmFL1 capable of initiating gene expression, the nucleotide sequence thereof being shown in SEQ ID NO. 4 or SEQ ID NO. 5. SEQ ID NO. 4 or SEQ ID NO. 5 is ligated to the reporter gene GUS to construct a vector which is transformed into rice, the GUS expression activity and expression pattern in the transgenic plants are detected and analyzed, by means of GUS-staining analysis in roots, stems, leaves and flowers of the transgenic plants, it was found that the pZmFL1 promoter drives GUS gene to express in plant anthers, and specifically express at the late stages of pollen development. It was shown that the promoter of SEQ ID NO:4 or 5 provided in the present invention is an anther-specific promoter.

The plant anther-specific promoter pZmFL1 provided in the present invention contains the nucleotide sequence shown in SEQ ID NO:4 or 5 in the sequence listing, or contains a nucleotide sequence with more than 90% similarity to the nucleotide sequence listed in SEQ ID NO:4 or 5, or contains a fragment of 100 or more than 100 consecutive nucleotides derived from the sequence of SEQ ID NO:4 or 5; and can drive the expression of the nucleotide sequence operably linked to the promoter in plant anthers. The expression vector, the transgenic cell line, and the host bacteria containing the sequence described above all belong to the protective scope of the present invention. The primer pairs for amplifying any nucleotide fragment of the promoter of SEQ ID NO:4 or 5 disclosed in the present invention also fall into the protective scope of the present invention.

The nucleotide sequence of the promoter provided in the present invention can also be used for isolating the corresponding sequences from other plants other than maize, especially for homologous cloning from other monocotyledons. The corresponding fragments are isolated and identified using techniques such as PCR and hybridization based on the sequence homology between the corresponding sequences and the promoter sequences listed herein or the homology between the corresponding sequences and the ZmFL1 gene herein. Therefore, the corresponding sequences identified according to their sequence similarity to the promoter sequence of SEQ ID NO:4 or 5 (or fragments thereof) listed herein are also included in the embodiments. The promoter region of the present embodiment can be isolated from any plants, including but not limited to, *Brassica*, maize, wheat, *sorghum, Crambe*, white mustard, castor bean, sesame, cottonseed, linseed, soybean, *Arabidopsis, Phaseolus*, peanut, alfalfa, oat, rapeseed, barley, lye, millet, dhurra, triticale, einkorn, Spelt, emmer, flax, grama grass, *Tripsacum*, teosinte, fescue, perennial ryegrass, sugarcane, cranberry, papaya, banana, safflower, oil palm, muskmelon, apple, cucumber, *Dendrobium*, gladiolus, chrysanthemum, Liliaceae, cotton, eucalyptus, sunflower, winter rape, sugar beet, coffee, yam, ornamental plants, and conifers, etc.

The "promoter" of the present invention refers to a DNA regulatory region, which generally includes a TATA box capable of directing RNA polymerase II to initiate RNA synthesis at the appropriate transcription start site of a specific encoding sequence. A promoter can also include other recognition sequences, and these recognition sequences are generally located upstream or at the 5' end of the TATA box, generally referred to as upstream promoter elements, which function in regulating transcription efficiency. A person skilled in the art should be aware that, although the nucleotide sequences directed to the promoter regions disclosed in the present invention have been identified, the isolation and identification of other unspecified regulatory elements located in the region upstream of the TATA box of the specific promoter region identified in the present invention also fall into the scope of the present invention. Therefore, the promoter region disclosed herein is generally further defined to include the upstream regulatory elements, for example, those elements used for regulating the spatial and temporal expression of the encoding sequence, as well as enhancers, etc. The promoter elements capable of expressing in a target tissue (for example, a male tissue) can be identified and isolated in the same manner and used together with other core promoters so as to verify that they preferentially express in male tissue. Core promoter is the minimal sequence required for initiating transcription, such as the sequence referred to as TATA box, which generally exists in a promoter of a gene encoding a protein. Therefore, alternatively, the upstream promoter of FL2 gene can be used in association with the core promoters of itself or from other sources.

A core promoter can be any one of the known core promoters, such as cauliflower mosaic virus 35S or 19S promoter (U.S. Pat. No. 5,352,605), ubiquitin promoter (U.S. Pat. No. 5,510,474), IN2 core promoter (U.S. Pat. No. 5,364,780) or figwort mosaic virus promoter.

The functions of the gene promoters can be analyzed by the following methods: operably linking a promoter sequence to a reporter gene to form a transformable construct, then transforming the construct into a plant, and validating the expression characteristics of the promoter through observing the expression of the reporter gene in various tissues and organs of the plants in the obtained transgenic progeny; or subcloning the construct described above into an expression vector used for transient expression assay, and detecting the function of the promoter or the regulatory region thereof through transient expression assay.

The selection of an appropriate expression vector used for testing the functions of the promoter or the regulatory region thereof will depend on the host and the methods for introducing the expression vector into the host, these methods are well known to a person of ordinary skill in the art. For eukaryotes, the regions in the vector include the regions for controlling transcription initiation and controlling processing. These regions are operably linked to a reporter gene, the reporter gene including YFP, UidA, GUS gene or luciferase. The expression vector containing a putative regulatory region located in a genomic fragment can be introduced into an intact tissue, such as staged pollen, or introduced into callus, so as to carry out function characterization.

Furthermore, pZmFL1 promoter of the present invention can be linked to a nucleotide sequence of non-FL1 gene to drive the expression of other heterologous nucleotide sequences. The promoter nucleotide sequence of the present invention and the fragment and variants thereof can be assembled together with heterologous nucleotide sequences in an expression cassette for expressing in a target plant, more particularly expressing in the male organ of the plant. The expression cassette has appropriate restriction sites for inserting the promoter and the heterologous nucleotide sequences. These expression cassettes can be used for carrying out genetic manipulation on any plants to obtain a desired corresponding phenotype.

The maize pZmFL1 promoter disclosed in the present invention can be used for driving the expression of the following heterologous nucleotide sequences to render the transformed plants the male-sterile phenotype. The heterologous nucleotide sequences can encode enzymes facilitating the degradation of carbohydrates, carbohydrate-modification enzymes, amylase, debranching enzyme and pectinase, and more particularly like α-amylase gene, auxin, rot B, cytotoxin gene, diphtheria toxin, DAM methylase, and avidin; and alternatively can be selected from a prokaryotic regulatory system, and can also be a dominant male-sterile gene.

In certain embodiments, as for the nucleic acid operably linked downstream of the promoter of the present invention, wherein the nucleic acid can be a structural gene, a regulatory gene, an antisense sequence of a structural gene, an antisense sequence of a regulatory gene or a small RNA capable of interfering the expression of an endogenous gene, which all of them operably linked to the promoter disclosed herein.

In the fifth aspect of the present invention, the present invention also provides an expression cassette which comprises:

(a) a promoter SEQ ID NO:4 or 5 of the fourth aspect of the present invention; and (b) nucleic acids, which is operably linked downstream of the promoter SEQ ID NO:4 or 5 of the present invention.

The expression cassette of the present invention along the 5'-3' transcription direction contains the promoter SEQ ID NO:4 or 5 of the present invention, a nucleic acid operably linked downstream to the promoter SEQ ID NO:4 or 5 of the present invention, and optionally transcription and translation termination regions (for example, transcription termination elements or polyadenylation signals). The expression cassette of the present invention can also contain a replication origin required for replication in bacteria (for example, ORI region derived from pBR322 or P15A ori), and elements required for Agrobacterium tumefaciens T-DNA transfer (for example, the left border and/or right border of T-DNA). Other components may be contained in the expression cassette of the present invention include enhancers, introns, multiple cloning sites, operator genes, repressor binding sites, transcription factor binding sites, etc. Exemplary enhancers include enhancer elements from CaMV 35S promoter, octopine synthase gene, rice actin I gene, maize alcohol dehydrogenase gene, maize stunt I gene, TMV Ω element, and yeast promoter. Virus leader sequence can also be used as an element with enhancer effect, such as the leader sequence from tobacco mosaic virus (TMV), maize chlorotic mottle virus (MCMV) and alfalfa mosaic virus (AMV) and the like. Exemplary plant introns include introns from genomic sequences of Adh 1, bronze 1, actin 1, and actin 2, as well as introns from the sucrose synthase gene.

As for the nucleic acid operably linked downstream to the promoter SEQ ID NO:4 or 5 of the present invention, wherein the nucleic acid can be a structural gene, a regulatory gene, an antisense sequence of a structural gene, an antisense sequence of a regulatory gene, or a small RNA capable of interfering the expression of an endogenous gene, all of which are operably linked to the promoter disclosed herein.

In particular, the fertility regulating gene SEQ ID NO:1, 2, 6, 8 or 10 provided in the present invention can be constructed downstream to promoter SEQ ID NO:4 or 5 so as to drive the specific expression of the fertility regulating gene in anthers; alternatively, by means of RNAi, a DNA vector driven by promoter SEQ ID NO:4 or 5 that is capable of silencing SEQ ID NO: 1, 2, 6, 8 or 10 gene, is constructed, and thus male-sterile mutants of SEQ ID NO: 1, 2, 6, 8 or 10 gene are obtained.

As seen above, any nucleic acid sequences described above can be operably linked to the promoter sequence of SEQ ID NO:4 or 5 of the present invention and expressed in plants.

The anther-specific expression promoter provided in the present invention can be used for the specific expression of exogenous gene in anthers so as to avoid adverse effects caused by the constitutive expression of the exogenous gene in other tissues of the plant, and can also be used for the functional analysis and characterization of genes involved in plant pollen growth and development; it can be used for constructing a male sterile line and a restorer line; and it can be used in pollen abortion experiment so as to avoid biosafety problems caused by plant transgene flow and pollen escape, and has great significance in the creation of the male sterility line and the restorer line in plants.

In the sixth aspect of the present invention, the expression cassette provided in the present invention can be inserted into a plasmid, a cosmid, a yeast artificial chromosome, a bacterial artificial chromosome, or any vector suitable for transformation into host cells. Preferable host cells are bacterial cells, especially the bacterial cells used for cloning or storing polynucleotides or the bacterial cells used for transforming plant cells, for example, *Escherichia coli*, *Agrobacterium tumefaciems*, and *Agrobacterium rhizogenes*. The expression cassettes or vectors can be inserted into the genome of the transformed plant cells when the host cells are plant cells. Insertion can be either precise or random. Preferably, insertion is implemented by homologous recombination and so on. Additionally, the expression cassettes or vectors can be maintained extrachromosomally. The expression cassettes or vectors of the present invention can exist in nuclei, chloroplasts, mitochondria, and/or plastids of plant cells. Preferably, the expression cassettes or vectors of the present invention are inserted into the chromosomal DNA in plant cell nuclei.

In the seventh aspect, the present invention provides a method for generating plants, which comprises:

(1) constructing expression cassettes provided in the second aspect or the fifth aspect of the present invention;

(2) introducing the expression obtained in (1) into plant cells;

(3) regenerating transformed plants; and (4) selecting for the transgenic plants; and (5) optionally, proliferating the plants obtained in (4) to obtain progenies.

The transgenic plants of the present invention are prepared by a transformation method known to a person in the field of plant biotechnology. Any methods can be used for transforming the recombinant expression vectors into plant cells to produce the transgenic plants of the present invention. Transformation methods may include direct and indirect transformation methods. Suitable direct methods include polyethylene glycol-induced DNA uptake, liposome-mediated transformation, biolistic introduction of DNA, electroporation, microinjection, and the like. In a particular embodiment of the present invention, the present invention uses an *Agrobacterium*-based transformation technology (see Horsch R B et al. (1985) Science 225:1229; White F F, Vectors for Gene Transfer in Higher Plants, Transgenic Plants, vol. 1, Engineering and Utilization, Academic Press, 1993, pp. 15-38; Jenes B et al. Techniques for Gene Transfer, Transgenic Plants, vol. 1, Engineering and Utilization, Academic Press, 1993, pp. 128-143, etc.). *Agrobacterium* strain (such as *Agrobacterium tumefaciems* or *Agrobacterium rhizogenes*) contains plasmids (Ti or Ri plasmid) and T-DNA elements. The plasmids and elements are transferred to plants after transformation using *Agrobacterium*, and T-DNA is integrated into the genome of plant cells. T-DNA can locate in Ri-plasmid or Ti-plasmid, or independently be contained in so-called binary vectors. *Agrobacterium*-mediated transformation method is described in "for example". *Agrobacterium*-mediated transformation is most suitable for dicotyledons, but also suitable for monocotyledons. The plant transformation with *Agrobacterium* is described in "for example". Transformation may result in transient or stable transformation and expression. Although the nucleotide sequences of the present invention can be inserted and introduced into any plants and plant cells within these wide-ranging species, the nucleotide sequences are especially suitable for crop plant cells.

The present invention also includes the use of the disclosed FL1 gene and the promoter thereof; and in embodiments of some application, FL1 gene and the promoter thereof provided in the present invention can be utilized for the proliferation and maintenance of the male sterility line, which is obtained by mutation of FL1 gene or other similar fertility-related genes.

In particular, the proliferation and maintenance of the male sterility line described above refer to that a homozygous recessive nuclear male-sterile mutant is used as a transformation acceptor material, and three closely-linked target genes in tandem are transformed into the sterile mutant acceptor plants. The three target genes are fertility restoring gene, pollen-lethal gene, and selective marker gene, respectively. Among them, the fertility restoring gene can restore fertility to the transformed acceptor which is sterile; the pollen-lethal gene can inactivate pollens that containing the transformed exogenous gene, i.e., the pollens lose fertilization capability; and the selective gene can be used for sorting transgenic seeds from non-transgenic seeds, and the sorted non-transgenic seeds are used as the male sterile line for producing hybrids, whereas transgenic seeds are used as the maintainer line for continuously and stably producing the sterile line.

More particularly, according to an embodiment of the present invention, the recessive nuclear sterile zmfl1/zmfl1 mutant of maize can be used as a transformation acceptor material, and three closely-linked target genes are transformed into the sterile line, wherein the fertility restoring gene ZmFL1 can restore the fertility of the transformed acceptor; the pollen-lethal gene Zm-PA can inactivate the pollen containing transformed exogenous gene, i.e., the pollen loses fertilization capability; and the fluorescent color sorting gene RFP (r) can be used for sorting transgenic seeds from non-transgenic seeds, and the sorted non-transgenic seeds are used as a sterile line for producing hybrids, whereas the transgenic seeds are used as the maintainer line for continuously and stably producing the sterile line. This technology, utilizing biotechnology to produce non-transgenic products, solves the bottleneck problem during the process of maize hybrid seed production.

As compared to prior arts, the present invention has the following beneficial effects: the present invention provides a maize pollen development gene and a male sterile line produced based on the mutation of the gene, and the sterile line has stable fertility which is not affected by environmental conditions; Mutator insertions at both sites found on the gene sequence can cause stable male-sterile phenotypes. The gene and the sterile line produced by the mutation of the gene provide resources for the hybrid breeding of maize, and also provides essential elements for constructing the third generation of hybrid breeding system; the male-sterile line produced through the mutation of the gene is used to produce hybrid seeds, which makes significant breakthroughs and improves the existing "three-line" and "two-line" hybridization technology.

BRIEF DESCRIPTION OF THE DRAWINGS

FIG. 10 is the sequence alignment of the protein encoded by ZmFL1 gene to the homologous proteins predicted in the genomes of rice, sorghum, and Arabidopsis, in which the amino acid sequence of Maize is shown in SEQ ID NO:3; the amino acid sequence of Rice is shown in SEQ ID NO:7; the amino acid sequence of Sorghum is shown in SEQ ID NO:9; and the amino acid sequence of Arabidopsis thaliana is shown in SEQ ID NO:11.

DETAILED DESCRIPTION OF THE EMBODIMENTS

Figure 1:
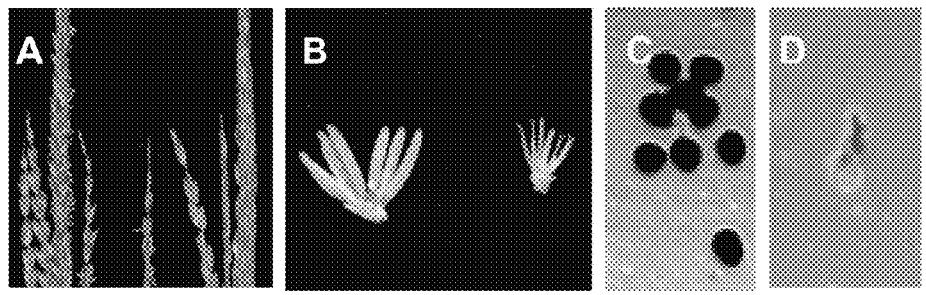
FIG. 1 is comparison of anthers at the pollination stage and the maturation stage of the wild-type individual plant and the zmfl1 individual sterile mutant plant.

The examples of the present invention will be described in details hereinafter, the examples are implemented on the premises of the technical solutions of the present invention and give detailed embodiments and specific operational processes, but the protective scope of the present invention is not limited to the following examples.

Embodiment 1. Screening of Male-sterile Mutant

Mutator (Mu) is to date the most active and mutagenic transposon discovered in plants with unique genetic characteristics including high forward mutation rate, and the tendencies of inserting into gene-rich regions and low-copy sequence regions, etc.; and it plays an important role in research of the functional gene and in constructing mutant library of maize. A mutant library was constructed utilizing a material carrying Mutator9 and a Chinese elite maize inbred line Zong 31. The two materials were hybridized to obtain $M_1$ seeds, and the $M_1$ were planted and allowed to self to obtain $M_2$ seeds. $M_1$ plants were harvested in single ear and threshed, and seeds from each ear were used as a strain. 20 grains from each $M_2$ strain were planted in Hunan Agricultural University campus in March, 2009. Two lines were planted with 10 grains each line using single grain sowing. It was found that one of the 1000 planted strains has three sterile plants and nine fertile plants, sister cross was allowed for maintenance, and the sterile line was named as zmfl1.

Embodiment 2. Genetic Analysis of Zmfl1 Male-sterile Mutant

Four maize inbred lines were utilized to hybridize to the sterile individual plant zmfl1 obtained in example 1. Field fertility of the four $F_1$ populations during pollination stage were identified and the four $F_1$ populations all showed fertile phenotypes; $F_1$ individual plants were selfed, harvested in individual plants and ears ($F_2$) were sowed; field fertility of the four $F_2$ populations during pollination stage were identified, and the fertility segregation occurred in all of the four $F_2$ populations, and the segregation ratio of normal plants to sterile plants conformed to 3:1 segregation ratio (Table 1) of the Mendel's law of segregation; therefore, it can be inferred that the male-sterile phenotype is controlled by a single recessive nuclear gene with two alleles.

TABLE 1

Segregation ratio of the fertile plants to the sterile plants of the four $F_2$ populations

| Combination | Total plants | Normal plants | Sterile plants | Normal/Sterile theoretical value (3:1) | $\chi^2$ |
|---|---|---|---|---|---|
| Zheng 58 | 266 | 208 | 58 | 199.5:66.5 | 1.28 |
| Chang 7-2 | 205 | 164 | 41 | 153.75:51.25 | 2.47 |
| B73 | 199 | 151 | 48 | 149.25:49.75 | 0.04 |
| MO17 | 321 | 231 | 90 | 240.75:80.25 | 1.58 |

Embodiment 3. Fertility Stability Analysis of Zmfl1 Male-sterile Mutant

The male sterile plants zmfl1 in example 1 were sister-crossed with the fertile plants individually. The obtained sterile plants parents and their segregating progenies were sowed respectively at three different ecological sites Sanya (Hainan province), Changsha (Hunan province) and Beijing, and the fertility for each individual plant was analysed during the pollination stage. The sterile plants with the same male-sterile phenotype as their parents were acquired in each population, which demonstrated that the sterile phenotypes controlled by the fertility gene were not influenced by temperature and lighting conditions. In particular, the fertility performance of plants for hybridization between the sister plants of the parents at different times and different locations are shown in Table 2, and the fertility performance of the segregating populations a different times and different locations are shown in Table 3:

TABLE 2

Fertility performance for sister cross of parents at different times and different locations

| Sowing time | Sowing location | Fertile plants | Sterile plants |
|---|---|---|---|
| March 2009 | Changsha, Hunan | 9 | 3 |
| September 2009 | Changsha, Hunan | 5 | 19 |
| December 2009 | Sanya, Hainan | 3 | 10 |

TABLE 2-continued

Fertility performance for sister cross of parents at different times and different locations

| Sowing time | Sowing location | Fertile plants | Sterile plants |
|---|---|---|---|
| March 2010 | Changsha, Hunan | 2 | 8 |
| September 2010 | Changsha, Hunan | 6 | 9 |
| December 2010 | Sanya, Hainan | 5 | 5 |
| May 2011 | Beijing | 11 | 8 |

Embodiment 3 Fertility Performance for Segregating Populations at Different Times and Different Locations

| Sowing time | Sowing location (populations) | Fertile plants | Sterile plants |
|---|---|---|---|
| March 2011 | Changsha, Hunan (MO17-$F_2$) | 231 | 90 |
| October 2011 | Sanya, Hainan (Zheng 58-$F_2$) | 1312 | 411 |
| May 2012 | Beijing (Zheng 58-$F_2$) | 208 | 58 |
| May 2012 | Beijing (Chang 7-2-$F_2$) | 164 | 41 |
| May 2012 | Beijing (B73-$F_2$) | 151 | 48 |

Embodiment 4. Phenotypic Analysis of the Reproductive Organs of the Zmfl1 Male-sterile Mutant The fertile individual plants and zmfl1 sterile individual plants were investigated during the anther pollination stage. It was found that, the anthers of the wild-type individual plants (FIG. 1, A left) were capable of exposing from inner and outer glumes and shedding pollen; the anthers of the sterile-mutant individual plants (FIG. 1, A right) were incapable of exposing from inner and outer glumes and shedding pollen; the investigation during anther maturation stage found that, the anthers of the wild-type individual plants (FIG. 1, B left) were plump and yellow, the anthers of the sterile-mutant individual plants (FIG. 1, B right) were wilted, relatively small and reddish-brown; the investigation results for iodine-potassium iodide staining of pollen showed that the pollen of the wild-type individual plants was round and black-brown (FIG. 1, C), whereas in the sterile-mutant individual plants there were only residual materials that resulted from the degradation of the anther walls and microspores, without pollen grains (FIG. 1, D).

Figure 2:
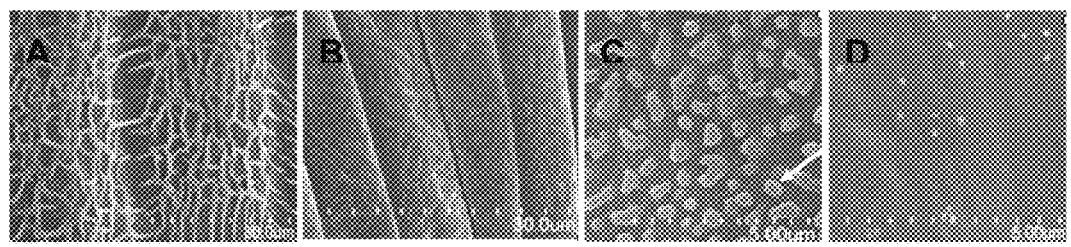
FIG. 2 is comparison of anther at the maturation stage of the wild-type individual plant and the zmfl1 individual sterile mutant plant (results from scanning electron microscope).

The scanning electron microscopy analysis of the inner and outer surfaces of the anthers of the wild-type individual plants and the zmfl1 sterile-mutant individual plants during maturation stage showed that the outer surface of the anthers of the wild-type individual plants was dense (FIG. 2, A), and the outer surface of the anthers of the sterile-mutant individual plants was smooth (FIG. 2, B); a large quantity of Ubisch bodies were arranged on the inner surface of the anthers of the wild-type individual plants (FIG. 2, C), and the inner surface of the anthers of the sterile-mutant individual plants was smooth and had no Ubisch bodies (FIG. 2, D).

Figure 3:
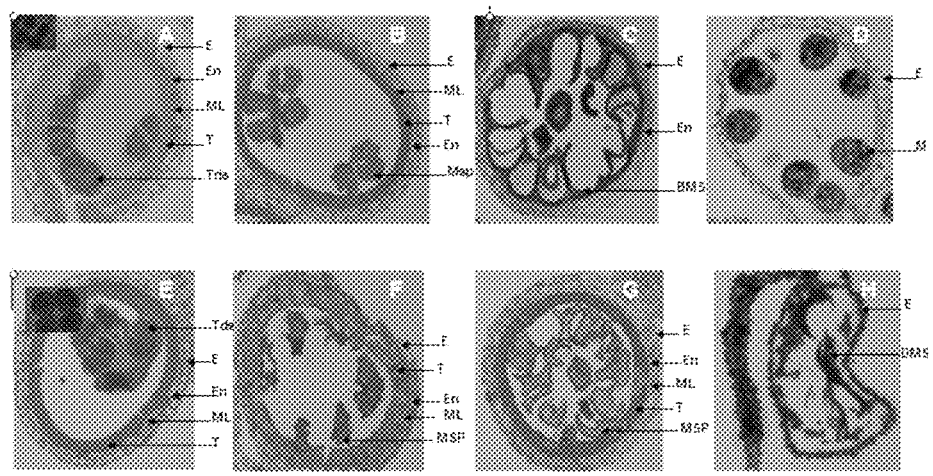
FIG. 3 is analytical results of the semithin section of the anthers of the wild-type individual plant and the zmfl1 individual sterile mutant plant.

The analysis of the semi-thin sections of the anthers of the wild-type plants and the zmfl1 sterile-mutant plants showed that: at the tetrad stage, the anthers of the wild-type individual plants (FIG. 3, A) and the sterile-mutant individual plants (FIG. 3, E) were substantially not different from the tetrads; at the uninucleate microspore stage, the cytoplasm of the anther tapetum of the wild-type individual plants (FIG. 3, B) was condensed and darkened in color, whereas the tapetum of the sterile-mutant individual plants (FIG. 3, F) was slightly expanded and the color didn't deepen as compared to the tetrad stage, with abnormal shape of the mutant microspores; from the late uninucleate microspore stage to the binucleate pollen grain stage, the anther tapetum of the wild-type plants (FIG. 3, C) almost degraded completely, the microspores were vacuolated and simultaneously nuclear division occurred to form binucleate or trinucleate pollen grains, whereas the tapetum of the sterile-mutant plants (FIG. 3, G) was larger than that of the wild type, with less degradation, less microspore vacuolization, and abnormal microspores which began to degrade; at the mature pollen grain stage, the pollen grains of the anthers of the wild-type plants (FIG. 3, D) were filled with starch and lipids, whereas there were merely residual materials from the degradation of the microspores in the anthers of the sterile-mutant plants (FIG. 3, H).

Figure 4:
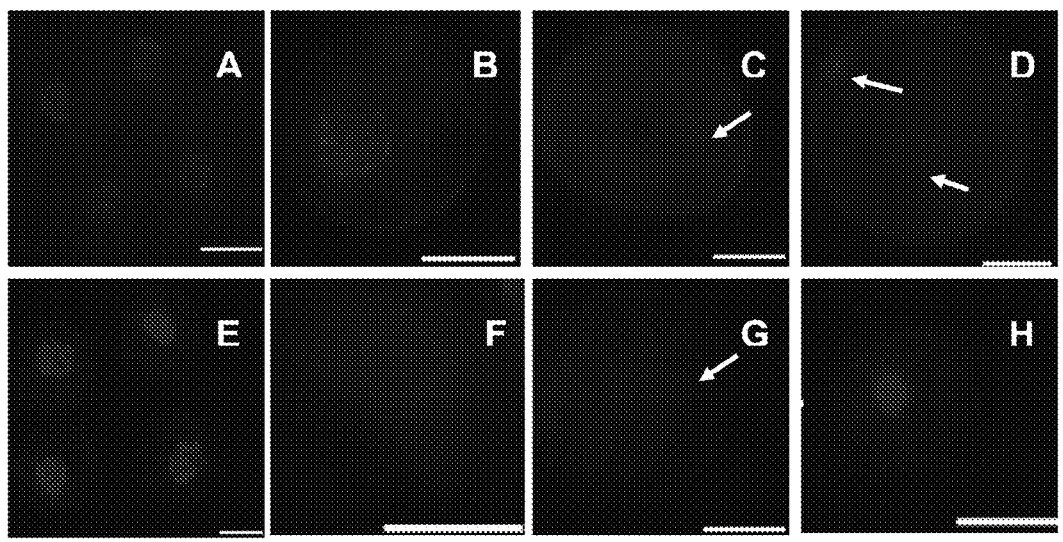
FIG. 4 is the pollen developmalent processes of the wild-type individual plant and the zmfl1 individual sterile mutant plant with DAPI staining.

The pollen development processes of the wild-type individual plants and the zmfl1 sterile-mutant individual plants were observed with DAPI staining: at the tetrad stage, the tetrads of the wild-type individual plants (FIG. 4, A) and the tetrads of the sterile mutants (FIG. 4, E) were not different; at the early uninucleate microspore stage, the microspores of the sterile-mutant individual plants (FIG. 4, F) were in abnormal shape as compared to the microspores of the wild-type individual plants (FIG. 4, B); at the late uninucleate microspore stage, the microspores of the sterile-mutant individual plants (FIG. 4, G) had begun to degrade as compared to the microspores of the wild-type individual plants (FIG. 4, C); at the binucleate pollen grain stage: the microspores of the sterile mutants (FIG. 4, H) had been degraded obviously as compared to the microspores of the wild type (FIG. 4, D).

Figure 5:
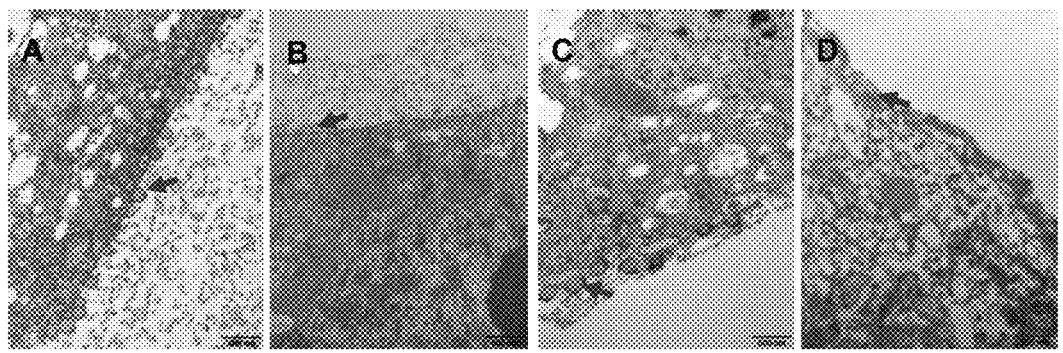
FIG. 5 is the developmental process of Ubisch body and pollen grain wall of the wild-type individual plant and the zmfl1 individual sterile mutant plant observed with transmission electron microscope.

The Ubisch bodies and the pollen grain wall development of the wild-type individual plants and the zmfl1 sterile-mutant individual plants were observed using a transmission electron microscope: at the tetrad stage, the Ubisch bodies on the inner surface of the tapetum of the wild type (FIG. 5, A; as indicated by the arrow) were slightly more and in slightly larger than the Ubisch bodies on the inner surface of the tapetum of the zmfl1 mutants (FIG. 5, B; as indicated by the arrow); at the early uninucleate microspore stage, the Ubisch bodies on the inner surface of the tapetum of the wild type (FIG. 5, C; as indicated by the arrow) began to accumulate sporopollenin precursor, whereas the Ubisch bodies on the inner surface of the tapetum of the zmfl1 mutants (FIG. 5, D, as indicated by the arrow) seemed to have been degraded.

Figure 6:
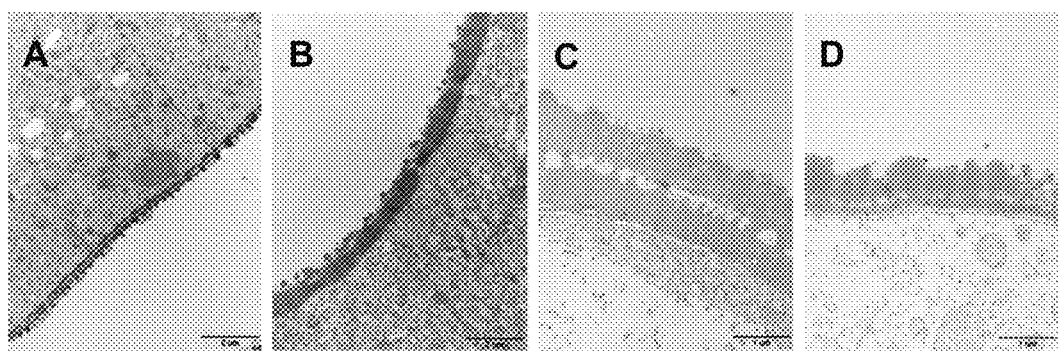
FIG. 6 is the structural analysis of the pollen from uninucleate microspore stage to binucleate pollen grain stage of the wild-type individual plant and the zmfl1 individual sterile mutant plant.

The uninucleate microspore stage of the pollen of the wild-type individual plants and the zmfl1 sterile-mutant individual plants was analyzed. It was found that the outer wall of the pollen grains of the wild-type individual plants clearly is composed of an outer layer, an inner layer, and a prismatic layer (FIG. 6, A), whereas the sterile-mutant individual plants only contain an inner layer and a small amount of sporopollenin materials filled thereon (FIG. 6, B); from the late uninucleate microspore stage to the binucleate pollen grain stage, the outer wall layer of the pollen grains of the wild-type individual plants was thickened (FIG. 6, C), while the outer wall of the pollen grains of the sterile-mutant individual plants still had the inner layer and the small amount of sporopollenin materials filled thereon, instead of three distinct layers (FIG. 6, D).

Embodiment 5. Cloning of Zmfl1 Male-sterile Mutant Gene

The zmfl1 sterile mutant was used as the female parent and hybridized with a wild-type inbred line Zheng 58, and the $F_1$ generation was selfed to construct the $F_2$ population. Using the identification standards of whether the anthers expose or not, the color of the anthers, and whether there is pollen during the pollination stage of maize, individual plants with the sterile mutant phenotype were screened from the F₂ population to carry out the preliminary mapping and fine mapping. Totally 2757 individual plants with the sterile mutant phenotype were obtained by screening. The target gene was defined between the markers S1 and S11 by preliminary mapping (FIG. 7).

According to the genome-wide physical map of B73, the genomic sequence between the two markers S1 and S11 was obtained, and this sequence was used to develop novel SSR markers and STS markers. Screening of the polymorphic markers was conducted for the sterile mutants, Zheng 58 and their combined F₁, and finally 10 pairs of polymorphic molecular markers were selected for further fine mapping, which were S, S2, S3, S4, S5, S6, S7, S8, S9 and S10, respectively (FIG. 7).

For the F₂ populations of Zheng 58 and the sterile mutants, according to the phenotypes of the recombinant individuals, genotype analysis was respectively carried out for these recombinant individuals using the developed markers. It was found that the numbers of recombinants in which the genomic region between the markers S2, S3, S4, S5 and the target gene had exchanged had decreased to 29 plants, 25 plants, 16 plants and nine plants, respectively; the numbers of recombinants between the markers S10, S9, S8 and the target gene had decreased to 14 plants, 13 plants and 11 plants, respectively, and the recombinant individuals on both sides were different; and the numbers of the recombinants between the markers S, S6, S7 and the target gene were zero. According to the law of diminishing of recombinant individuals and three-point test, the target gene was eventually mapped to the region flanked by markers S5 and S8, with nine recombinant individuals and 11 recombinant individuals, respectively. The actual physical distance between the two markers is approximately 300 kb (FIG. 7).

Figure 7:
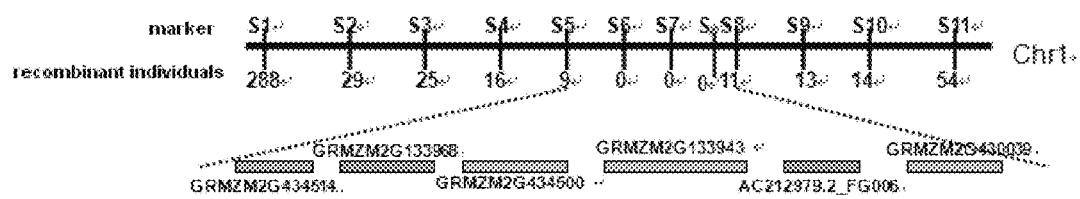
FIG. 7 is map-based cloning of the male-sterile mutant gene.

Gene annotation and bioinformatics analysis of the candidate genes were carried out for the 300 kb interval in which the target gene is located, and it was found that there were six candidate genes in this region (FIG. 7).

Figure 8:
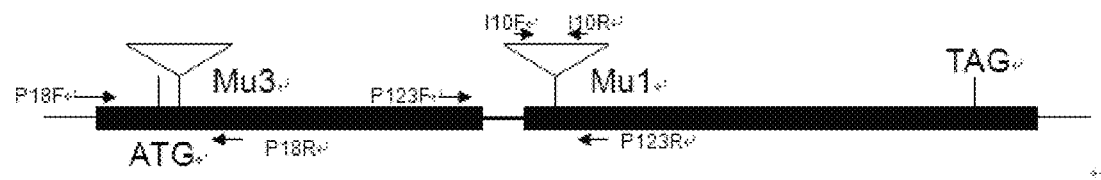
FIG. 8 is structure of the sterile mutant candidate gene.

By gene sequencing, it was found that Mutator1 transposon was inserted (FIG. 8) in the second exon (chr1: 80,964,768) of the candidate wild-type male fertility restorer gene GRMZM2G434500 (Chromosome 1: 80,963,525-80,966,109), and the mutant phenotype was consistent with the genotype. The candidate wild-type male fertility restorer gene GRMZM2G434500 was named as ZmFL1, its genomic DNA sequence is shown in SEQ ID NO:1; its encoding cDNA. sequence is shown in SEQ ID NO:2; and its encoded amino acid sequence is shown in SEQ ID NO:3.

Embodiment 6. Allelic Mutation of Zmfl1 Male-sterile Mutant Gene

A mutant line of the gene GRMZM2G434500 was obtained from MAIZEGDB. Sequencing of the gene region of the mutant line revealed a Mutator3 insertion in the first exon (chr1: 80,963,850) of ZmFL1 gene, and the phenotype thereof was consistent with the genotype.

Figure 9:
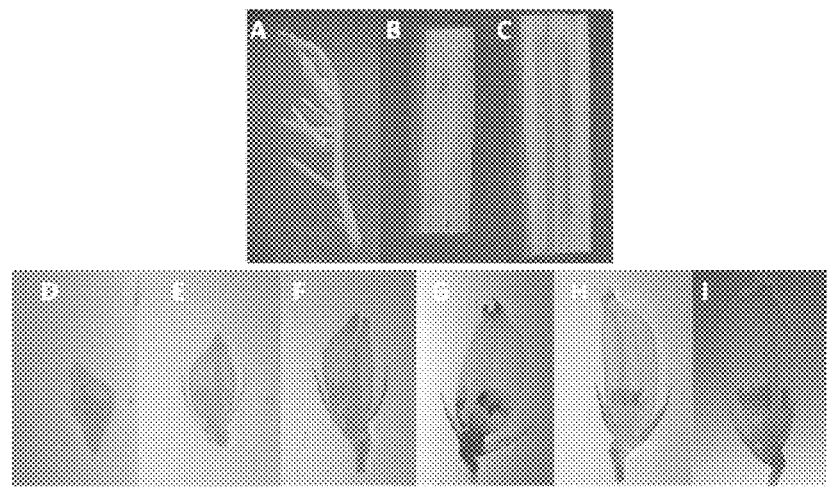
FIG. 9 is the expression of GUS in various tissues and organs of rice driven by pZmFL1 promoter, wherein A is root; B is stem; C is leaf; and D-I are staining of rice flowers at various stages.

Embodiment 7. Construction and Functional Analysis of the Expression Vector of ZmFL1 Promoter Construction of the expression vector of ZmFL1 gene promoter: by means of maize genome amplification, two promoter fragments were respectively obtained: the length of a promoter fragment was 875 bp, the nucleotide sequence thereof being shown in SEQ ID NO:4; the length of the other promoter fragment was 2500 bp, the nucleotide sequence thereof being shown in SEQ ID NO:5. Plant expression vectors for the functional characterization of the promoter were obtained with the two fragments ligated to GUS respectively. The vectors were transformed into the calli of wild-type rice through an Agrobacterium-mediated method, and 12 and 18 transgenic rice plants were obtained through regeneration and screening, respectively. The expression pattern of pZmFL1 promoter was obtained by analyzing the activity of β-galactosidase, and the roots, stems, leaves and flowers of the transgenic plants were analyzed by GUS staining. It was found that the GUS gene driven by the pZmFL1 promoter mainly expressed in anthers, more particularly expressedat the late pollen development stage, and its GUS staining results were shown in FIG. 9.

Figure 10:
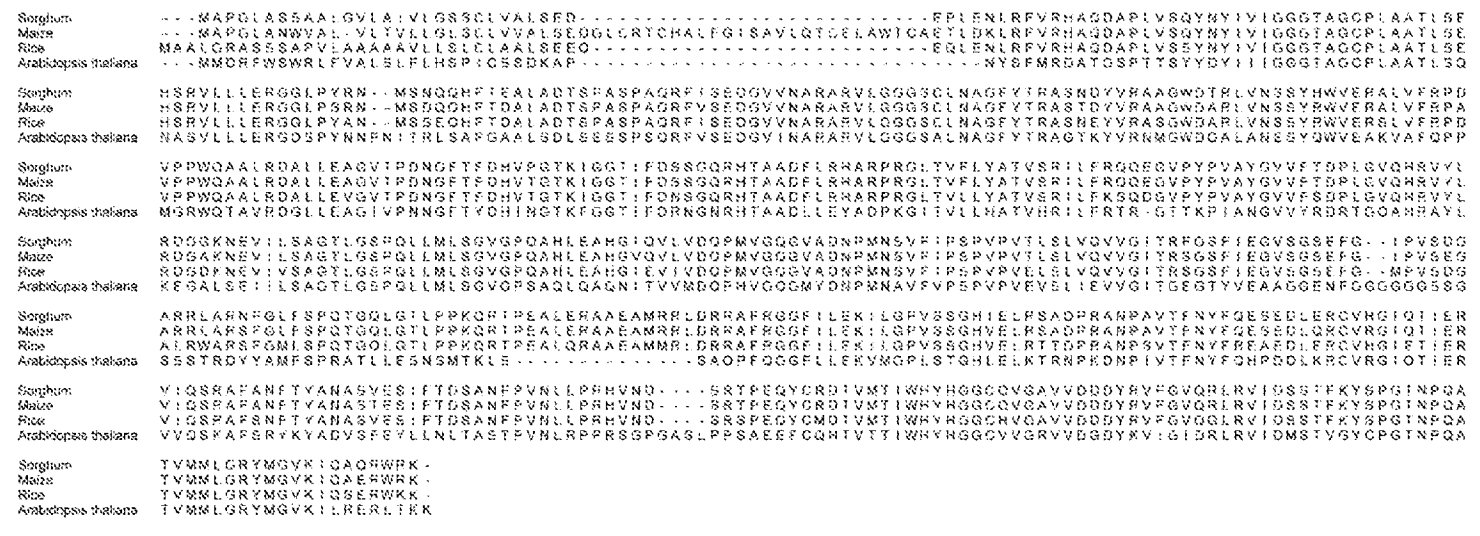

Embodiment 8. Sequence Alignment of the Protein Encoded by ZmFL1 Gene to the Homologous Proteins Predicted in the Genomes of Rice, Sorghum, and Arabidopsis The complete sequence of the protein encoded by maize ZmFL1 gene was used as the template to search the NCBI Database utilizing Protein Blast Tool to obtain the homologous proteins in the genomes of rice, sorghum, and Arabidopsis; alignment of these proteins showed that all the homologous proteins from different plants had very similar and conserved sequences with very high homology among one another (FIG. 10), which demonstrated that this protein is conserved in biological functions and plays a very important role in the development of male floral organs of the plants. Among them, the genomic sequence of the homologous gene OsFL1 in rice is shown in SEQ ID NO:6, and the encoded amino acid thereof is shown in SEQ ID NO:7; the genomic sequence of the homologous gene SbFL1 in sorghum is shown in SEQ ID NO:8, and the encoded amino acid thereof is shown in SEQ ID NO:9; the genomic sequence of the homologous gene AtFL1 in Arabidopsis is shown in SEQ ID NO:10, and the encoded amino acid thereof is shown in SEQ ID NO:11.

Embodiment 9. Application of ZmFL1 Gene in New Generation of Hybrid Breeding Technology ZmFL1 gene can be used in the new generation of hybrid breeding technology, and the core concept of the technology lies in that: the recessive nuclear male-sterile mutant of maize is used as the transformation acceptor material, three closely-linked target genes are transformed into the sterile mutant, wherein the fertility restoring gene can restore fertility to the transformed acceptor; the pollen-lethal gene can inactivate the pollen containing the exogenous gene, i.e., the pollen loses fertilization capability; and the selective gene can be used for sorting transgenic seeds from non-transgenic seeds, the sorted non-transgenic seeds being the male sterile line, while the transgenic seeds being the maintainer line. The male sterile line can set seeds through pollination by the maintainer line, which allows proliferation of the male sterile line. In the meantime, the maintainer line can proliferate continuously through selfing. This technology, utilizing biotechnology to produce non-transgenic products, solves the manual or mechanical emasculation problems in maize hybrid seed production, omits the step of manual emasculation or mechanical emasculation, provides seeds with higher quality and purity for the growers, and saves labor costs.

According to the above principles, more particularly, maize ZmFL1 gene was used to construct a plant expression vector. The expression vector contained three expression cassettes: Zm-AA1 (pollen-lethal gene), ZmFL1 (fertility restoring gene), and RFP (red fluorescent color sorting gene). The fertility of the obtained transformant plants was restored when the expression cassette was transformed into the maize zmfl1 homozygous male-sterile mutant. The restored transformants have the following characteristics: ZmFL1 fertility restoring gene can restore the fertility of the transformed acceptor; Zm-AA1 pollen-lethal gene can inactivate the pollen containing the exogenous gene, i.e., the pollen loses fertilization capability; and RFP selective gene can be used for sorting transgenic seeds from non-transgenic seeds, the sorted non-transgenic seeds being the male sterile line, and the transgenic seeds being the maintainer line. Thus, a new generation of hybrid breeding technology system was established.

According to the above principles, an expression vector was constructed by using the maize ZmFL1 gene by the inventors. Before constructing the plant expression vector for maize, firstly, the three expression cassettes that each contain a pollen-lethal gene Zm-PA, a fertility restoring gene ZmFL1, and a selective gene RFP(r) in the expression vector were transformed into maize individually by the inventors. Furthermore, the function of each expression cassette was verified. The results showed that the three expression cassettes all worked well when transformed into maize individually and achieved the expected and designed effects.

Further, a new generation of maize expression vector for hybrid breeding technology was constructed through assembly of the following DNA elements by the inventors:

1) pCAMBIA2300 vector was used as the basis;
2) the gene expression cassette LTP2:RFP(r)-PINII: the open reading frame of RFP(r) gene (SEQ ID NO:12) was linked between LTP2 promoter (SEQ ID NO:13) and PINII terminator (SEQ ID NO:14) to create a RFP(r) gene expression cassette (LTP2:RFP(r):PINII);
3) the ZmFL1 gene expression cassette, which was composed of the target gene ZmFL1, as well as the promoter and terminator thereof, wherein the promoter sequence of ZmFL1 gene is shown in SEQ ID NO:5, the terminator sequence thereof is shown in SEQ ID NO:16, the genomic DNA sequence of ZmFL1 gene from the start codon to the stop codon is shown in SEQ ID NO:15, and the amino acid sequence of the protein encoded by its nucleotide sequence is shown in SEQ ID NO:3;
4) the gene expression cassette PG47:ZM-BT1:ZM-PA:IN2-1, containing the open reading frame of the target gene ZM-PA (the nucleotide sequence thereof being shown in SEQ ID NO:17) was ligated downstream of promoter PG47 (the nucleotide sequence thereof being shown in SEQ ID NO:18) and transit peptide ZM-BT1 (the nucleotide sequence thereof being shown in SEQ ID NO:19) and upstream of terminator IN2-1 (the nucleotide sequence thereof being shown in SEQ ID NO:20).

The constructed expression vector described above was transformed into maize to obtain positive transgenic maize plants.

Inspection of pollen fertility of the transgenic maize plants: the obtained single-copy transgenic maize (containing homozygous zmfl1 recessive sterile loci) plants described above were analyzed and it was found that there was no obvious morphological difference between the transgenic plants and non-transgenic control plants, but their pollen fertilities were substantially different. The pollen stainability of the transgenic plant material and that of the wild-type maize were analyzed simultaneously.

The method used is as follows: at the flowering stage of maize, individual plants were randomly sampled from the transgenic maize plants and the wild-type control plants thereof, respectively. One spikelet was taken from the staminate inflorescence of each individual plant, one floret was taken from the spikelet, and one anther was taken from the floret and placed in the center of a glass slide. One drop of 1% $I_2$-KI solution was added, a pair of tweezers and a dissecting needle were used to release the pollen. The sample was covered by a cover glass, observed under a microscope, and the number of stainable pollens and the total number of the pollens were counted, the stainable pollen in dark blue being fertile and the non-stained pollen being abortive. The pollen stainability analysis showed that the stainable pollen garains of the control plants accounted for 98%-100%; whereas the ratio of the normal pollens (stainable) to the abortive pollens (non-stained) in the multiple randomly-sampled transgenic plants approximated 1:1, which indicated that the constructed transgenic strain can produce equal amount of pollen grains carrying the exogenous gene and pollen grains without the exogenous gene, i.e., the introduced maize expression vector described above can deactivate 50% of the pollen grains of the transgenic strain. The results indicated that the vector provided in the present invention can achieve the expected pollen-deactivating function.

Analysis on separation of fluorescent seeds and non-fluorescent seeds of the transgenic maize plants: the seeds set on the $T_1$ generation ears of the obtained single-copy transgenic maize plants described above (containing homozygous zmfl1 recessive sterile loci) underwent the segregation ratio analysis, the results showed that all of these seeds showed a 1:1 segregation ratio of fluorescent seeds and non-fluorescent seeds, i.e., the fluorescent seeds carrying the exogenous gene and the non-fluorescent seeds without the exogenous gene exhibited a 1:1 ratio, which indicated that the various elements of the vector provided in the present invention were expressed well as a whole, and the purposes of creation and reproduction of the sterile line can be achieved; wherein ZmFL1 gene can restore the fertility to the male-sterile mutant acceptor, and the expression of Zm-PA gene and RFP gene can achieve the expected pollen-deactivating function and the seed screening marker function, respectively.

The invention claimed is:

1. An isolated nucleotide sequence comprising the nucleotide sequence of SEQ ID NO:2 or the full length complementary sequence of SEQ ID NO:2.

2. The isolated nucleotide sequence of claim 1, consisting of SEQ ID NO:2.

3. An expression cassette, comprising the nucleotide sequence of claim 1 operably linked to a promoter sequence.

4. The expression cassette of claim 3, wherein the promoter sequence comprises SEQ ID NO:4 or SEQ ID NO:5.

5. An expression vector, comprising the expression cassette of claim 3.

6. An engineered bacterium, wherein the engineered bacterium contains the expression vector of claim 5.

7. An expression vector, comprising the nucleotide sequence SEQ ID NO:4 or SEQ ID NO:5, operably linked to the nucleotide sequence of claim 1.

8. An engineered bacterium, wherein the engineered bacterium contains the expression vector of claim 7.

9. A method for expressing a target nucleotide sequence in a plant, the method comprises: introducing the expression vector of claim 7 into the plant, wherein the target nucleotide sequence is expressed.

10. The method of claim 9, wherein the plant is a monocotyledon.

11. The method of claim 10, wherein the monocotyledon is Gramineae.

12. The method of claim 11, wherein the Gramineae is rice, maize or *sorghum*.

\* \* \* \* \*